(12) United States Patent
MacDonald et al.

(10) Patent No.: US 8,847,005 B2
(45) Date of Patent: Sep. 30, 2014

(54) GENETICALLY MODIFIED MAJOR HISTOCOMPATIBILITY COMPLEX MICE

(71) Applicant: Regeneron Pharmaceuticals, Inc., Tarrytown, NY (US)

(72) Inventors: Lynn MacDonald, White Plains, NY (US); Andrew J. Murphy, Croton-on-Hudson, NY (US); Naxin Tu, Pleasantville, NY (US); Cagan Gurer, Valhalla, NY (US); Vera Voronina, Thornwood, NY (US); Sean Stevens, San Francisco, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/661,116

(22) Filed: Oct. 26, 2012

(65) Prior Publication Data

US 2013/0111616 A1 May 2, 2013

Related U.S. Application Data

(60) Provisional application No. 61/552,584, filed on Oct. 28, 2011.

(51) Int. Cl.
| | | |
|---|---|---|
| A01K 67/027 | (2006.01) | |
| A61K 39/395 | (2006.01) | |
| A61K 39/40 | (2006.01) | |
| C07K 14/74 | (2006.01) | |

(52) U.S. Cl.
CPC ....... *A01K 67/0278* (2013.01); *C07K 14/70539* (2013.01)
USPC ............................. 800/18; 800/14; 424/133.1

(58) Field of Classification Search
CPC ..................... A01K 67/0278; C07K 14/70539
USPC .................................. 800/18, 14; 424/133.1
See application file for complete search history.

(56) References Cited

U.S. PATENT DOCUMENTS

| | | | |
|---|---|---|---|
| 5,413,923 A | 5/1995 | Kucherlapati et al. | |
| 5,416,260 A | 5/1995 | Koller et al. | |
| 5,574,205 A | 11/1996 | Kucherlapati et al. | |
| 5,644,065 A | 7/1997 | Benoist et al. | |
| 5,859,312 A | 1/1999 | Littman et al. | |
| 5,965,787 A | 10/1999 | Luthra et al. | |
| 6,002,066 A | 12/1999 | Leung et al. | |
| 6,139,835 A | 10/2000 | Kucherlapati et al. | |
| 6,150,584 A | 11/2000 | Kucherlapati et al. | |
| 6,270,772 B1 | 8/2001 | Burrows et al. | |
| 6,372,955 B1 | 4/2002 | Karlsson et al. | |
| 6,514,752 B1 | 2/2003 | Kucherlapati et al. | |
| 6,586,251 B2 | 7/2003 | Economides et al. | |
| 6,596,541 B2 | 7/2003 | Murphy et al. | |
| 6,815,171 B2 | 11/2004 | Burrows et al. | |
| 7,105,348 B2 | 9/2006 | Murphy et al. | |
| 7,265,218 B2 | 9/2007 | Burrows et al. | |
| 7,294,754 B2 | 11/2007 | Poueymirou et al. | |
| 7,339,089 B2 | 3/2008 | Gotoh | |
| 7,663,017 B2 | 2/2010 | Lone et al. | |
| 7,745,690 B2 | 6/2010 | Kanazawa et al. | |
| 2003/0093818 A1 | 5/2003 | Belmont et al. | |
| 2005/0050580 A1 | 3/2005 | Gotoh et al. | |
| 2005/0066375 A1 | 3/2005 | Thiam et al. | |
| 2005/0114910 A1 | 5/2005 | Lone et al. | |
| 2006/0107339 A1 | 5/2006 | Gotoh et al. | |
| 2007/0209083 A1 | 9/2007 | Thiam et al. | |
| 2009/0328240 A1 | 12/2009 | Sing et al. | |
| 2010/0011450 A1 | 1/2010 | Garcia et al. | |
| 2010/0138938 A1 | 6/2010 | Garcia et al. | |
| 2011/0067121 A1 | 3/2011 | Lone et al. | |

FOREIGN PATENT DOCUMENTS

| | | |
|---|---|---|
| EP | 0437576 B1 | 7/2002 |
| EP | 1878342 A1 | 1/2008 |
| EP | 1878798 A1 | 1/2008 |
| EP | 0950707 B1 | 2/2009 |
| EP | 1017721 B1 | 2/2009 |
| EP | 1409646 B1 | 6/2012 |
| WO | 9101140 A1 | 2/1991 |
| WO | 9211753 A1 | 7/1992 |
| WO | 9305817 A1 | 4/1993 |
| WO | 9503331 A1 | 2/1995 |
| WO | 9732603 A1 | 9/1997 |
| WO | 9824893 A2 | 6/1998 |
| WO | 02059263 A2 | 8/2002 |
| WO | 2005/004592 A2 | 1/2005 |
| WO | 2008010099 A2 | 1/2008 |
| WO | 2008010100 A2 | 1/2008 |
| WO | 2009114400 A1 | 9/2009 |
| WO | 2012039779 A1 | 3/2012 |

OTHER PUBLICATIONS

Woods et al., 1994, J. Exp. Med., vol. 180, p. 173-181.*
Houdebine, L-M., 2002, Journal of Biotechnology, vol. 98, p. 145-160.*
Goldman et al., 2004, Med Sci Monit, vol. 10, No. 11, RA274-285.*
Shinobara et al., 2007, Transgenic research, vol. 16, p. 333-339.*
Sigmund, C., Jun. 2000, Arterioscler. Thromb. Vasc. Biol., p. 1425-1429.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Wooldridge et al. (2010) MHC Class I Molecules with Superenhanced CD8 Binding Properties Bypass the Requirement for Cognate TCR Recognition and Nonspecifically Activate CTLs, J. Immunol. 184:3357-66.

(Continued)

*Primary Examiner* — Shin Lin Chen
(74) *Attorney, Agent, or Firm* — Margarita Zippin; Brenda Herschbach Jarrell; Rolando Medina

(57) ABSTRACT

The invention provides genetically modified non-human animals that express a humanized MHC II protein (humanized MHC II α and β polypeptides), as well as embryos, cells, and tissues comprising the humanized MHC II protein. Also provided are constructs for and methods of making the genetically modified non-human animals. Methods of using the genetically modified non-human animals to study various aspects of the human immune system are provided.

16 Claims, 12 Drawing Sheets

(56) References Cited

OTHER PUBLICATIONS

Connolly et al. (1988) The Lyt-2 Molecule Recognizes Residues in the Class I alpha3 Domain in Allogeneic Cytotoxic T Cell Responses, J. Exp. Med. 168:325-41.
Sanders et al. (1991) Mutations in CD8 that Affect Interactions with HLA Class I and Monoclonal Anti-CD8 Antibodies, J. Exp. Med. 174:371-79.
Gao et al. (1997) Crystal structure of the complex between human CD88alpha-alpha and HLA-A2, Nature 387:630-34.
Salter et al. (1989) Polymorphism in the alpha3 domain of HLA-A molecules affects binding to CD8, Nature 338:345-47.
Vitiello et al. (1991) Analysis of the HLA-restricted Influenza-specific Cytotoxic T Lymphocyte Response in Transgenic Mice Carrying a Chimeric Human-Mouse Class I Major Histocompatibility Complex, J. Exp. Med. 173:1007-15.
Potter et al. (1989) Substitution at residue 227 of H-2 class I molecules abrogates recognition by CD8-dependent, but not CD8-independent, cytotoxic T lymphocytes, Nature 337:73-75.
Irwin et al. (1989) Species-restricted interactions between CD8 an the alpha3 domain of class I influence the magnitude of the xenogeneic response, J. Exp. Med. 170:1091-1101.
Wagner et al. (1994) Ligation of MHC Class I and Class II Molecules Can Lead to Heterologous Desensitization of Signal Transduction Pathways That Regulate Homotypic Adhesion in Human Lymphocytes, J. Immunol. 152:5275-87.
Gruda et al. (2007) Intracellular Cysteine Residues in the Tail of MHC Class I Proteins Are Crucial for Extracellular Recognition by Leukocyte Ig-Like Receptor 1, J. Immunol. 179:3655-3661.
Lynch et al. (2009) Novel MHC Class I Structures on Exosomes, J. Immunol. 183:1884-91.
Gur et al. (1997) Structural Analysis of Class I MHC Molecules: The Cytoplasmic Domain Is Not Required for Cytoskeletal Association, Aggregation and Internalization, Mol. Immunol. 34:125-32.
Lizee et al. (2003) Control of dendritic cell cross-presentation by the major histocompatibility complex class I cytoplasmic domain, Nature Immunol. 4:1065-73.
Basha et al.(2008) MHC Class I Endosomal and Lysosomal Trafficking Coincides with Exogenous Antigen Loading in Dendritic Cells, PLoS ONE 3:e3247, 11 pages.
Rodriguez-Cruz et al. (2011) Natural Splice Variant of MHC Class I Cytoplasmic Tail Enhances Dendritic Cell-Induced CD8+ T-Cell Responses and Boosts Anti-Tumor Immunity, PLoS ONE 6:e22939, 10 pages.
Shankarkumar (2004) The Human Leukocyte Antigen (HLA) System, Int. J. Hum. Genet. 4:91-103.
Marsh et al. (2010) Nomenclature for factors of the HLA system, 2010, Tissue Antigens 75:291-455.
Holdsworth et al. (2009) The HLA dictionary 2008: a summary of HLA-A, -B, -C -DRB1/3/4/5, and -DQB1 alleles and their association with serologically defined HLA-A, -B, -C, -DR, and -DQ antigens, Tissue Antigens 73:95-170.
Festing et al. (1999) Revised nomenclature for strain 129 mice, Mammalian Genome 10:836.
Auerbach et al. (2000) Establishment and Chimera Analysis of 129/SvEV- and C57BL/6-Derived Mouse Embryonic Stem Cell Lines, BioTechniques 29:1024-1032.
Perarnau et al. (1988) Human B2-microglobulin specifically enhances cell-surface expression of HLA class I molecules in transfected murine cells, J. Immunol. 141:1383-89.
Tishon et al. (2000) Transgenic Mice Expressing Human HLA and CD8 Molecules Generate HLA-Restricted Measles Virus Cytotoxic T Lymphocytes of the Same Specificity as Humans with Natural Measles Infection, Virology 275:286-93.
Gussow et al. (1987) The Human B2-Microglobulin Gene. Primary Structure and Definition of the Transcriptional Unit, J. Immunol. 139:3132-38.
Josson et al. (2011) B2 microglobulin induces epithelial to mesenchymal transition and confers cancer lethality and bone metastasis in human cancer cells, Cancer Res. 71:1-11.
Koller et al. (1990) Normal Development of Mice Deficient in B2M, MHC Class I Proteins, and CD8+ T Cells. Science 248:1227-30.
Allen et al. (1986) B2-Microglobulin is not required for cell surface expression of the murine class I histocompatibility antigen H-2Db or of a truncated H-2Db, Proc. Natl. Acad. Sci. USA 83:7447-51.
Quinn et al. (1997) Virus-Specific, CD8+ Major Histocompatibility Complex Class I-Restricted Cytotoxic T Lymphocytes in Lymphocytic Choriomeningitis Virus-Infected B2-Microglobulin-Deficient Mice, J. Virol. 71:8392-96.
Cooper et al. (2007) An Impaired Breeding Phenotype in Mice with a Genetic Deletion of Beta-2 Microglobulin and Diminished MHC Class I Expression: Role in Reproductive Fitness, Biol. Reprod. 77:274-79.
Chamberlain et al. (1988) Tissue-specific and cell surface expression of human major histocompatibility complex class I heavy (HLA-B7) and light (B2-microglobulin) chain genes in transgenic mice, Proc. Natl. Acad. Sci. USA 86:7690-94.
Pajot et al. (2004) A mouse model of human adaptive immune functions: HLA-A2.1/HLA-DR1-trasngenic H-2 class I-/class II-knock-out mice, Eur. J. Immunol. 34:3060-69.
Pittet et al. (2003) Alpha3 Domain Mutants of Peptide/MHC Class I Multimers Allow the Selective Isolation of High Avidity Tumor-Reactive CD8 T Cells, J. Immunol. 171:1844-49.
Fooksman et al. (2009) Cutting Edge: Phosphotidylinositol 4, 5-Bisphosphate Concentration at the APC Side of the Immunological Synapse Is Required for Effector T Cell Function, J. Immunol. 182:5179-82.
Pettersen et al. (1998) The TCR-Binding Region of the HLA Class I alpha2 Domain Signals Rapid Fas-Independent Cell Death: A Direct Pathway for T Cell-Mediated Killing of Target Cells? J. Immunol. 160:4343-52.
Woodle et al. (1997) Anti-Human Class I MHC Antibodies Induce Apoptosis by a Pathway That Is Distinct from the Fas Antigen-Meidated Pathway, J. Immunol. 158:2156-64.
Bernabeu et al. (1984) B2-Microglobulin from serum associates with MHC class I antigens on the surface of cultured cells, Nature 308:642-45.
Laface et al. (1995) Human CD8 Transgene Regulation of HLA Recognition by Murine T Cells, J. Exp. Med. 182:1315-25.
Takaki et al. (2006) HLA-A*0201-Restricted T Cells from Humanized NOD Mice Recognize Autoantigens of Potential Clinical Relevance to Type I Diabetes, J. Immunol. 176:3257-65.
De Bakker et al. (2006) A high-resolution HLA and SNP haplotype map for disease association studies in the extended human MHC, Nature Genetics 38:1166-72.
De Bakker et al. (2006) A high-resolution HLA and SNP haplotype map for disease association studies in the extended human MHC, Nature Genetics Online Supplement, 33 pages.
International MHC and Autoimmunity Genetics Network (IMAGEN) (2009) Mapping of multiple susceptibility variants within the MHC region for 7 immune-mediated diseases, Proc. Natl. Acad. Sci. USA 106:18680-85.
Poueymirou et al. (2007) F0 generation mice fully derived from gene-targeted embryonic stem cells allowing immediate phenotypic analyses, Nature Biotechnology 25:91-99.
Lie and Petropoulos (1998) Advances in quantitative PCR technology: 5' nuclease assays, Curr. Opin. Biotechnol. 9:43-48.
Valenzuela et al. (2003) High-throughput engineering of the mouse genome coupled with high-resolution expression analysis, Nature Biotechnology 21:652-59.
Willcox et al. (2003) Crystal structure of HLA-A2 bound to LIR-1, a host and viral major histocompatibility complex receptor, Nature Immunol. 4:913-19.
Shiroishi et al. (2003) Human inhibitory receptors Ig-like transcript 2 (ILT2) and ILT4 compete with CD8 for MHC class I binding and bind preferentially to HLA-G, Proc. Natl. Acad. Sci. USA 100:8856-61.
Kirwan et al. (2005) Killer Cell Ig-Like Receptor-Dependent Signaling by Ig-Like Transcript 2 (ILT2/CD85j/LILRB1/LIR-1), J. Immunol. 175:5006-15.
Rubio et al. (2004) Cross-linking of MHC class I molecules on human NK cells inhibits NK cell function, segregates MHC I from the NK cell synapse, and induces intracellular phosphotyrosines, J. Leukoc. Biol. 76:116-24.

(56) References Cited

OTHER PUBLICATIONS

Betser-Cohen et al. (2010) The Association of MHC Class I Proteins with the 2B4 Receptor Inhibits Self-Killing of Human NK Cells, J. Immunol. 184:2761-68.
Rosano et al. (2005) The three-dimensional structure of B2 microglobulin: Results from X-ray crystallography, Biochim. Biophys. Acta 1753:85-91.
Shultz et al. (2007) Humanized mice in translational biomedical research, Nature Rev. 7:118-30.
Chung S. et al., Functional three-domain single-chain T-cell receptors, Proc. Natl. Acad. Sci. USA, 91:12654-12658 (1994).
Li L.P. et al., Transgenic mice with a diverse human T cell antigen receptor repertoire, Nature Med., 16(9):1029-1035 (2010).
Linnenbach A, Huebner K, Croce CM, DNA-transformed murine teratocarcinoma cells: regulation of expression of simian virus 40 tumor antigen in stem versus differentiated cells. Proc Natl Acad Sci U S A. 77(8):4875-9 (1980).
Mendez M.J., et al., Functional transplant of megabase human immunoglobulin loci recapitulates human antibody response in mice, Nat Genet. 15(2):146-56 (1997).
Mombaerts P. et al., Spontaneous Development of Inflammatory Bowel Disease in T Cell Receptor Mutant Mice, Cell, 75:275-282 (1993).
Taylor L.D. et al., Human immunoglobulin transgenes undergo rearrangement, somatic mutation and class switching in mice that lack endogenous IgM, Int Immunol. 6(4):579-91 (1994).
Wagner S.D. et al., The diversity of antigen-specific monoclonal antibodies from transgenic mice bearing human immunoglobulin gene miniloci, Eur J Immunol. 24(11):2672-81 (1994).
Wagner SD et al., Antibodies generated from human immunoglobulin miniloci in transgenic mice, Nucleic Acids Res. 22(8):1389-93 (1994).
Street et al. (2002) Limitations of HLA-transgenic mice in presentation of HLA-restricted cytotoxic T-cell epitopes from endogenously processed human papillomavirus type 16 E7 protein, Immunology 106:526-36.
Firat et al. (2002) Comparative analysis of the CD8+ T cell repertoires of H-2 class I wild-ype/HLA-2.1 and H-2 class I knockout/HLA-A2.1 transgenic mice, International Immunol. 14:925-34.
Benmohamed et al. (2000) Induction of CTL Response by a Minimal Epitope Vaccine in HLA-A*0201/DR1 Transgenic Mice: Dependence on HLA Class II Restricted TH Response, Hum. Immunol. 61:764-79.
Wang and Reinherz (2001) Structural basis of T cell recognition of peptides bound to MHC molecules, Molecular Immunology 38:1039-49.
Kumanovics et al. (2003) Genomic Organization of the Mammalian MHC, Annu. Rev. Immunol. 21:629-57.
Murphy, Travers, and Walport, Janeway's Immunobiology (7th ed. 2008), Garland Science, pp. 125-138 and 196-213.
Nickerson et al. (1990) Expression of HLA-B27 in Transgenic Mice Is Dependent on the Mouse H-2D Genes, J. Exp. Med. 172:1255-1261.
Ureta-Vidal et al. (1999) Phenotypical and Functional Characterization of the CD8 + T Cell Repertoire of HLA-A2.1 Transgenic, H-2Kb°Db° Double Knockout Mice, J. Immunol. 163:2555-2560.
Johansson et al. (2005) Natural killer cell education in mice with single or multiple major histocompatibility complex class I molecules, J. Exp. Med. 201:1145-1155.
Pascolo et al. (1997) HLA-A2.1—restricted Education and Cytolytic Activity of CD8+ T Lymphocytes from from Beta 2 Microglobulin (B2m) HLA-A2.1 Monochain Transgenic H-2Db B2m Double Knockout Mice, J. Exp. Med. 185:2043-2051.
Vugmeyster et al. (1998) Major histocompatibility complex (MHC) class I KbDb −/− deficient mice possess functional CD8+ T cells and natural killer cells. Proc. Natl. Acad. Sci USA, 95:12492-12497.
Smiley et al. (1996) Truncation of the class II beta-chain cytoplasmic domain influences the level of class II/ invariant chain-derived peptide complexes, Proc. Natl. Acad. Sci. USA 93:241-44.

Ostrand-Rosenberg et al. (1991) Abrogation of Tumorigenicity by MHC Class II Antigen Expression Requires the Cytoplasmic Domain of the Class II Molecule, J. Immunol. 147:2419-22.
El Fakhry et al. (2004) Delineation of the HLA-DR Region and the Residues Involved in the Association with the Cytoskeleton, J. Biol. Chem. 279:18472-80.
Dolan et al. (2004) Invariant Chain and the MHC Class II Cytoplasmic Domains Regulate Localization of MHC Class II Molecules to Lipid Rafts in Tumor Cell-Based Vaccines, J. Immunol. 172:907-14.
Shin et al. (2006) Surface expression of MHC class II in dendritic cells is controlled by regulated ubiquitination, Nature 444:115-18.
De Gassart et al. (2008) MHC class II stabilization at the surface of human dendritic cells is the result of maturation-dependent MARCH I down-regulation, Proc. Natl. Acad. Sci. USA 105:3491-96.
Cosson and Bonifacino (1992) Role of Transmembrane Domain Interactions in the Assembly of Class II MHC Molecules, Science 258:659-62.
Wong and Wen (2004) What can the HLA transgenic mouse tell us about autoimmune diabetes?, Diabetologia 47:1476-87.
Taneja and David (1998) HLA Transgenic Mice as Humanized Mouse Models of Disease and Immunity, J. Clin. Invest. 101:921-26.
Raffegerst et al. (2009) Diverse Hematological Malignancies Including Hodgkin-Like Lymphomas Develop in Chimeric MHC Class II Transgenic Mice, PLoS ONE 4:e8539, 12 pages.
Ito et al. (1996) HLA-DR4-IE Chimeric Class II Transgenic, Murine Class II-Deficient Mice Are Susceptible to Experimental Allergic Encephalomyelitis, J. Exp. Med. 183:2635-44.
Lee et al. (1982) Sequence of an HLA-DR alpha-chain cDNA clone and intron-exon organization of the corresponding gene, Nature 299:750-52.
Woods et al. (1994) Human Major Histocompatibility Complex Class II-Restricted T Cell Responses in Transgenic Mice, J. Exp. Med. 180:173-81.
Fugger et al. (1994) Expression of HLA-DR4 and human CD4 transgenes in mice determines the variable region beta-chain T-cell repertoire and mediates an HLA-DR-restricted immune response, Proc. Natl. Acad. Sci. USA 91:6151-55.
Vignali et al. (1992) Species-specific Binding of CD4 to the Beta2 Domain of Major Histocompatibility Complex Class II Molecules, J. Exp. Med. 175:925-32.
Yamamoto et al. (1994) Functional Interaction between Human Histocompatibility Leukocyte Antigen (HLA) Class II and Mouse CD4 Molecule in Antigen Recognition by T Cells in HLA-DR and DQ Transgenic Mice, J. Exp. Med. 180:165-71.
Smiley et al. (1995) Transgenic mice expressing MHC class II molecules with truncated A-beta cytoplasmic domains reveal signaling-independent defects in antigen presentation, International Immunol. 7:665-77.
Fukui et al. (1997) Differential requirement of MHC class II molecules expressed on hematopoietic cells for positive selection of CD4+ thymocytes in TCRalpha-beta and TCRbeta transgenic mice, International Immunol. 9:1385-1391.
Ishimito et al. (1997) In Vitro and In Vivo Evidence for High Frequency of I-Ab-Reactive CD4+ T Cells in HLA-DQ or HLA-DRA Transgenic Mice Lacking Endogenous MHC Class I and/or Class II Expression, J. Immunol. 159:3717-3722.
Jakobovits (1994) Humanizing the mouse genome, Current Biology 4:761-63.
Madsen et al. (1999) A humanized model for multiple sclerosis using HLA-DR2 and a human T cell receptor, Nature Genetics 23:343-47.
Danner et al. (2011) Expression of HLA Class II Molecules in Humanized NOD.Rag1KO.1L2RgKO Mice is Critical for Development and Function of Human T and B Cells, PLoS One 6:e19826, 12 pages.
Altmann et al. (1995) The T Cell Response to HLA-DR Transgenic Mice to Human Myelin Basic Protein and other Antigens in the Presence and Absence of Human CD4, J. Exp. Med. 181:867-75.
Zijlstra et al. (1990) B2-Microglobulin deficient mice lack CD4-8+ cytolytic T cells, Nature 344:742-46.

* cited by examiner

```
                            SEQUENCE LISTING

<160> NUMBER OF SEQ ID NOS: 26

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
cagaacgcca ggctgtaac                                                    19

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
ggagagcagg gtcagtcaac                                                   20

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
caccgccact cacagctcct taca                                              24

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
gtgggcacca tcttcatcat tc                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
```

```
cttcctttcc agggtgtgac tc                                              22
```

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6

```
aggcctgcga tcaggtggca cct                                             23
```

<210> SEQ ID NO 7
<211> LENGTH: 17
<212> TYPE: DNA
<213> ORGANISM: Artificial Sequence
<220> FEATURE:
<223> OTHER INFORMATION: Synthetic

<400> SEQUENCE: 7

```
tgcggccgat cttagcc                                                    17
```

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8

```
ttgaccgatt ccttgcgg                                                   18
```

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9

```
acgagcgggt tcggcccatt c                                               21
```

<210> SEQ ID NO 10
<211> LENGTH: 140
<212> TYPE: DNA
<213> ORGANISM: Artificial Sequence
<220> FEATURE:
<223> OTHER INFORMATION: Synthetic

<400> SEQUENCE: 10

```
tttgtaaaca aagtctaccc agagacagat gacagacttc agctccaatg ctgattggtt     60
cctcacttgg gaccaaccct ctcgagtacc gttcgtataa tgtatgctat acgaagttat    120
atgcatccgg gtaggggagg                                                140
```

<210> SEQ ID NO 11
<211> LENGTH: 140
<212> TYPE: DNA
<213> ORGANISM: Artificial Sequence
<220> FEATURE:
<223> OTHER INFORMATION: Synthetic

<400> SEQUENCE: 11

```
cctcgacctg cagccctagg ataacttcgt ataatgtatg ctatacgaac ggtagagctc     60
cacaggcatt tgggtgggca gggatggacg gtgactggga caatcgggat ggaagagcat    120
```
agaatgggag ttagggaaga                                                    140

<210> SEQ ID NO 12
<211> LENGTH: 110
<212> TYPE: DNA
<213> ORGANISM: Artificial Sequence
<220> FEATURE:
<223> OTHER INFORMATION: Synthetic

<400> SEQUENCE: 12
tgctgattgg ttcctcactt gggaccaacc ctaagcttta tctatgtcgg gtgcggagaa        60
agaggtaatg aaatggcaca aggagatcac acacccaaac caaactcgcc                  110

<210> SEQ ID NO 13
<211> LENGTH: 96
<212> TYPE: DNA
<213> ORGANISM: Artificial Sequence
<220> FEATURE:
<223> OTHER INFORMATION: Synthetic

<400> SEQUENCE: 13
cacatcagtg aggctagaat aaattaaaat cgctaatatg aaaatgggga tttgtacctc        60
tgagtgtgaa ggctgggaag actgctttca agggac                                  96

<210> SEQ ID NO 14
<211> LENGTH: 150
<212> TYPE: DNA
<213> ORGANISM: Artificial Sequence
<220> FEATURE:
<223> OTHER INFORMATION: Synthetic

<400> SEQUENCE: 14
tccatcactt cactgggtag cacagctgta actgtccagc ctgggtaccg agctcggatc        60
cactagtaac ggccgccagt gtgctggaat tcgcccttga tcgagctccc tgggctgcag       120
gtggtgggcg ttgcgggtgg ggccggttaa                                        150

<210> SEQ ID NO 15
<211> LENGTH: 80
<212> TYPE: DNA
<213> ORGANISM: Artificial Sequence
<220> FEATURE:
<223> OTHER INFORMATION: Synthetic

<400> SEQUENCE: 15
atctccatca aagggcacc ggtataactt cgtataaggt atcctatacg aagttatatg         60
catggcctcc gcgccgggtt                                                    80

<210> SEQ ID NO 16
<211> LENGTH: 90
<212> TYPE: DNA
<213> ORGANISM: Artificial Sequence
<220> FEATURE:
<223> OTHER INFORMATION: Synthetic

<400> SEQUENCE: 16
ataacttcgt ataaggtatc ctatacgaag ttatctcgag tggcttacag gtaggtgcgt        60
gaagcttcta caagcacagt tgcccccctgg                                        90

<210> SEQ ID NO 17
<211> LENGTH: 90
<212> TYPE: DNA

<213> ORGANISM: Artificial Sequence
<220> FEATURE:
<223> OTHER INFORMATION: Synthetic

<400> SEQUENCE: 17
ctgtttcttc cctaactccc attctatgct cttccatccc gaccgcggcc caatctctct    60
ccactacttc ctgcctacat gtatgtaggt                                     90

<210> SEQ ID NO 18
<211> LENGTH: 80
<212> TYPE: DNA
<213> ORGANISM: Artificial Sequence
<220> FEATURE:
<223> OTHER INFORMATION: Synthetic

<400> SEQUENCE: 18
caaggtttcc tcctatgatg cttgtgtgaa actcggggcc ggccagcatt taacagtaca    60
gggatgggag cacagctcac                                                80

<210> SEQ ID NO 19
<211> LENGTH: 80
<212> TYPE: DNA
<213> ORGANISM: Artificial Sequence
<220> FEATURE:
<223> OTHER INFORMATION: Synthetic

<400> SEQUENCE: 19
gaaagcagtc ttcccagcct tcacactcag aggtacaaat ccccattttc atattagcga    60
ttttaattta ttctagcctc                                                80

<210> SEQ ID NO 20
<211> LENGTH: 80
<212> TYPE: DNA
<213> ORGANISM: Artificial Sequence
<220> FEATURE:
<223> OTHER INFORMATION: Synthetic

<400> SEQUENCE: 20
tcttccctaa ctcccattct atgctcttcc atcccgaccg cggcccaatc tctctccact    60
acttcctgcc tacatgtatg                                                80

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ctggcggctt gaagaatttg g                                              21

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
catgatttcc aggttggctt tgtc                                           24

<210> SEQ ID NO 23
<211> LENGTH: 26

```
<212> TYPE: DNA
<213> ORGANISM: Artificial Sequence
<220> FEATURE:
<223> OTHER INFORMATION: Synthetic

<400> SEQUENCE: 23
cgatttgcca gctttgaggc tcaagg                                          26

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
aggcttgggt gctccacttg                                                 20

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
gaccctggtg atgctggaaa c                                               21

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
caggtgtaaa cctctccact ccgagga                                         27
```

US 8,847,005 B2

GENETICALLY MODIFIED MAJOR HISTOCOMPATIBILITY COMPLEX MICE

CROSS-REFERENCE TO RELATED APPLICATION

This application claims benefit of priority to U.S. Provisional Application No. 61/552,584, filed Oct. 28, 2011, which is incorporated by reference herein in its entirety.

FIELD OF THE INVENTION

Present invention relates to a non-human animal, e.g., a rodent (e.g., a mouse or a rat) that is genetically engineered to express a humanized Major Histocompatibility Complex (MHC) class II protein, as well as embryos, tissues, and cells expressing the same. The invention further relates to methods for making a genetically modified non-human animal that expresses a humanized MHC II protein. Also provided are methods for using non-human animals, cells, and tissues that express a humanized MHC class II protein for identifying peptides that activate lymphocytes and engage T cells, and for developing human vaccines and other therapeutics.

BACKGROUND OF THE INVENTION

In the adaptive immune response, foreign antigens are recognized by receptor molecules on B lymphocytes (e.g., immunoglobulins) and T lymphocytes (e.g., T cell receptor or TCR). These foreign antigens are presented on the surface of cells as peptide fragments by specialized proteins, generically referred to as major histocompatibility complex (MHC) molecules. MHC molecules are encoded by multiple loci that are found as a linked cluster of genes that spans about 4 Mb. In mice, the MHC genes are found on chromosome 17, and for historical reasons are referred to as the histocompatibility 2 (H-2) genes. In humans, the genes are found on chromosome 6 and are called human leukocyte antigen (HLA) genes. The loci in mice and humans are polygenic; they include three highly polymorphic classes of MHC genes (class I, II and III) that exhibit similar organization in human and murine genomes (see FIG. 2 and FIG. 3, respectively).

MHC loci exhibit the highest polymorphism in the genome; some genes are represented by >300 alleles (e.g., human HLA-DRβ and human HLA-B). All class I and II MHC genes can present peptide fragments, but each gene expresses a protein with different binding characteristics, reflecting polymorphisms and allelic variants. Any given individual has a unique range of peptide fragments that can be presented on the cell surface to B and T cells in the course of an immune response.

Both humans and mice have class II MHC genes (see FIGS. 2 and 3). In humans, the classical MHC II genes are termed HLA-DP, HLA-DQ, and HLA-DR, whereas in mice they are H-2A and H-2E (often abbreviated as I-A and I-E, respectively). Additional proteins encoded by genes in the MHC II locus, HLA-DM and HLA-DO in humans, and H-2M and H-2O in mice, are not found on the cell surface, but reside in the endocytic compartment and ensure proper loading of MHC II molecules with peptides. Class II molecules consist of two polypeptide chains: α chain and β chain. The extracellular portion of the α chain contains two extracellular domains, α1 and α2; and the extracellular portion of the β chain also contains two extracellular domains, β1 and β2 (see FIG. 1). The α and the β chains are non-covalently associated with each other.

MHC class II molecules are expressed on antigen-presenting cells (APCs), e.g., B cells, macrophages, dendritic cells, endothelial cells during a course of inflammation, etc. MHC II molecules expressed on the surface of APCs typically present antigens generated in intracellular vesicles to CD4+ T cells. In order to participate in CD4+ T cell engagement, the MHC class II complex with the antigen of interest must be sufficiently stable to survive long enough to engage a CD4+ T cell. When a CD4+ T helper cell is engaged by a foreign peptide/MHC II complex on the surface of APC, the T cell is activated to release cytokines that assist in immune response to the invader.

Not all antigens will provoke T cell activation due to tolerance mechanisms. However, in some diseases (e.g., cancer, autoimmune diseases) peptides derived from self-proteins become the target of the cellular component of the immune system, which results in destruction of cells presenting such peptides. There has been significant advancement in recognizing antigens that are clinically significant (e.g., antigens associated with various types of cancer). However, in order to improve identification and selection of peptides that will provoke a suitable response in a human T cell, in particular for peptides of clinically significant antigens, there remains a need for in vivo and in vitro systems that mimic aspects of human immune system. Thus, there is a need for biological systems (e.g., genetically modified non-human animals and cells) that can display components of a human immune system.

SUMMARY OF THE INVENTION

A biological system for generating or identifying peptides that associate with human MHC class II proteins and chimeras thereof, and bind to CD4+ T cells, is provided. Non-human animals comprising non-human cells that express humanized molecules that function in the cellular immune response are provided. Humanized rodent loci that encode humanized MHC II proteins are also provided. Humanized rodent cells that express humanized MHC molecules are also provided. In vivo and in vitro systems are provided that comprise humanized rodent cells, wherein the rodent cells express one or more humanized immune system molecules.

Provided herein is a non-human animal, e.g., a rodent (e.g., a mouse or a rat) comprising in its genome a nucleotide sequence encoding a humanized MHC II complex, wherein a human portion of the humanized MHC II complex comprises an extracellular domain of a human MHC II complex, e.g., a humanized MHC II α extracellular domain and a humanized MHC II β extracellular domain.

In one aspect, provided herein is a non-human animal comprising at an endogenous MHC II α gene locus a nucleotide sequence encoding a chimeric human/non-human MHC II α polypeptide. In one embodiment, a human portion of such chimeric human/non-human MHC II α polypeptide comprises a human MHC II α extracellular domain. In one embodiment, the non-human animal expresses a functional MHC II complex on a surface of a cell of the animal. In one embodiment, the human MHC II α extracellular domain in the animal comprises human MHC II α1 and α2 domains; in one embodiment, a non-human portion of the chimeric human/non-human MHC II α polypeptide comprises transmembrane and cytoplasmic domains of an endogenous non-human MHC II α polypeptide. In one embodiment, the nucleotide sequence encoding a chimeric human/non-human MHC II α polypeptide is expressed under regulatory control of endogenous non-human MHC II α promoter and regulatory elements. In one embodiment, the human portion of the chimeric polypeptide is derived from a human HLA class II protein selected from the group consisting of HLA-DR, HLA-DQ, and HLA-DP, e.g., the human portion is derived from HLA-DR4 protein. The non-human animal may be a rodent, e.g., a mouse. In one aspect, the non-human animal comprising at an endogenous MHC II α gene locus a nucleotide sequence encoding a chimeric human/non-human MHC II α polypeptide further comprises at an endogenous MHC II β gene locus a nucleotide sequence encoding a chimeric human/non-human MHC II β polypeptide. Also provided herein is a method of making a genetically modified non-human animal comprising at an endogenous MHC II α gene locus a nucleotide sequence encoding a chimeric human/non-human MHC II α polypeptide. Such method may comprise replacing at an endogenous MHC II α gene locus a nucleotide sequence encoding an endogenous non-human MHC II α polypeptide with a nucleotide sequence encoding a chimeric human/non-human MHC II α polypeptide.

Also provided herein is a non-human animal comprising at an endogenous MHC II β gene locus a nucleotide sequence encoding a chimeric human/non-human MHC II β polypeptide. In one embodiment, a human portion of such chimeric human/non-human MHC II β polypeptide comprises a human MHC II β extracellular domain. In one embodiment, the non-human animal expresses a functional MHC II complex on a surface of a cell of the animal. In one embodiment, the human MHC II β extracellular domain in the animal comprises human MHC II β1 and β2 domains; in one embodiment, a non-human portion of the chimeric human/non-human MHC II β polypeptide comprises transmembrane and cytoplasmic domains of an endogenous non-human MHC II β polypeptide. In one embodiment, the nucleotide sequence encoding a chimeric human/non-human MHC II β polypeptide is expressed under regulatory control of endogenous non-human MHC II β promoter and regulatory elements. In one embodiment, the human portion of the chimeric polypeptide is derived from a human HLA class II protein selected from the group consisting of HLA-DR, HLA-DQ, and HLA-DP, e.g., the human portion is derived from HLA-DR4 protein. The non-human animal may be a rodent, e.g., a mouse. In one aspect, the non-human animal comprising at an endogenous MHC II β gene locus a nucleotide sequence encoding a chimeric human/non-human MHC II β polypeptide further comprises at an endogenous MHC II α gene locus a nucleotide sequence encoding a chimeric human/non-human MHC II α polypeptide. Also provided herein is a method of making a genetically modified non-human animal comprising at an endogenous MHC II β gene locus a nucleotide sequence encoding a chimeric human/non-human MHC II β polypeptide. Such method may comprise replacing at an endogenous MHC II β gene locus a nucleotide sequence encoding an endogenous non-human MHC II β polypeptide with a nucleotide sequence encoding a chimeric human/non-human MHC II β polypeptide.

In one aspect, a non-human animal is provided comprising at an endogenous MHC II gene locus a first nucleotide sequence encoding a chimeric human/non-human MHC II α polypeptide and a second nucleotide sequence encoding a chimeric human/non-human MHC II β polypeptide, wherein a human portion of the chimeric human/non-human MHC II α polypeptide comprises a human MHC II α extracellular domain and a human portion of the chimeric human/non-human MHC II β polypeptide comprises a human MHC II β extracellular domain. In one embodiment, the chimeric human/non-human MHC II α and β polypeptides form a functional chimeric MHC II complex (e.g., human/non-human MHC II complex) on a surface of a cell. In one embodiment, the human MHC II α extracellular domain comprises human α1 and α2 domains of human MHC II. In one embodiment, the human MHC II β extracellular domain comprises human β1 and β2 domains of human MHC II. In various aspects, the first nucleotide sequence is expressed under regulatory control of endogenous non-human MHC II α promoter and regulatory elements. In various aspects, the second nucleotide sequence is expressed under regulatory control of endogenous non-human MHC II β promoter and regulatory elements. In some embodiments, a non-human portion of the chimeric human/non-human MHC II α polypeptide comprises transmembrane and cytoplasmic domains of an endogenous non-human MHC II α polypeptide. In some embodiments, a non-human portion of the chimeric human/non-human MHC II β polypeptide comprises transmembrane and cytoplasmic domains of an endogenous non-human MHC II β polypeptide.

In various embodiments, the non-human animal is a rodent, and the human portions of the chimeric human/rodent MHC II α and β polypeptides comprise human sequences derived from HLA class II protein selected from the group consisting of HLA-DR, HLA-DQ, and HLA-DP. In some embodiments of the invention, the human portions of the chimeric human/rodent MHC II α and β sequences are derived from a human HLA-DR4 sequence; thus, the nucleotide sequence encoding the MHC II α extracellular domain is derived from a sequence of an HLA-DRα*01 gene, and the nucleotide sequence encoding the MHC II β extracellular domain is derived from a sequence encoding an HLA-DRβ1*04 gene.

In various embodiments of the invention, the first and the second nucleotide sequences are located on the same chromosome. In some aspects, the animal comprises two copies of the MHC II locus containing the first and the second nucleotide sequences, while in other aspects, the animal comprises one copy of the MHC II locus containing the first and the second nucleotide sequences. Thus, the animal may be homozygous or heterozygous for the MHC II locus containing the first and the second nucleotide sequences.

In some aspects, the chimeric MHC II α polypeptide and/or the chimeric MHC II β polypeptide is operably linked to a non-human leader sequence.

In one aspect, the genetically engineered non-human animal is a rodent. In one embodiment, the rodent is selected from the group consisting of a mouse and a rat. Thus, in some embodiments, non-human sequences of the chimeric MHC II α and β genes are derived from nucleotide sequences encoding mouse MHC II protein, e.g., a mouse H-2E protein. In one embodiment, the rodent (e.g., the mouse or the rat) of the invention does not express functional endogenous MHC II polypeptides from their endogenous loci. In one embodiment, wherein the rodent is a mouse, the mouse does not express functional endogenous H-2E and H-2A polypeptides from their endogenous loci.

Thus, in some embodiments, a mouse is provided comprising at an endogenous mouse MHC II locus a first nucleotide sequence encoding a chimeric human/mouse MHC II α polypeptide and a second nucleotide sequence encoding a chimeric human/mouse MHC II β polypeptide, wherein a human portion of the chimeric MHC II α polypeptide comprises an extracellular domain derived from an α polypeptide of a human HLA-DR4 protein and a human portion of the chimeric human/mouse MHC II β polypeptide comprises an extracellular domain derived from a β polypeptide of a human HLA-DR4 protein, wherein a mouse portion of the chimeric MHC II α polypeptide comprises transmembrane and cytoplasmic domains of a mouse H-2E α chain and a mouse portion of the chimeric MHC II β polypeptide comprises transmembrane and cytoplasmic domains of a mouse H-2E β chain, and wherein the mouse expresses a functional chimeric HLA-DR4/H-2E MHC II complex. In some aspects, the extracellular domain of the chimeric MHC II α polypeptide comprises human α1 and α2 domains; in some aspects, the extracellular domain of the chimeric MHC II β polypeptide comprises human β1 and β2 domains. In some embodiments, the first nucleotide sequence is expressed under regulatory control of endogenous mouse MHC II α promoter and regulatory elements, and the second nucleotide sequence is expressed under regulatory control of endogenous mouse MHC II β promoter and regulatory elements. In various embodiments, the mouse does not express functional endogenous MHC II polypeptides, e.g., H-2E and H-2A polypeptides, from their endogenous loci. In some aspects, the mouse comprises two copies of the MHC II locus containing the first and the second nucleotide sequences, while in other aspects, the mouse comprises one copy of the MHC II locus containing the first and the second nucleotide sequences.

Methods of making genetically engineered non-human animals (e.g., rodents, e.g., mice or rats) as described herein are also provided. In various embodiments, non-human animals (e.g., rodents, e.g., mice or rats) of the invention are made by replacing endogenous MHC II sequences with nucleotide sequences encoding chimeric human/non-human (e.g., human/mouse) MHC II α and β polypeptides. In one embodiment, the invention provides a method of modifying an MHC II locus of a rodent (e.g., a mouse or a rat) to express a chimeric human/rodent MHC II complex comprising replacing at the endogenous mouse MHC II locus a nucleotide sequence encoding a rodent MHC II complex with a nucleotide sequence encoding a chimeric human/rodent MHC II complex. In one aspect of the method, the nucleotide sequence encoding the chimeric human/rodent MHC II complex comprises a first nucleotide sequence encoding an extracellular domain of a human MHC II α chain and transmembrane and cytoplasmic domains of a rodent MHC II α chain and a second nucleotide sequence encoding an extracellular domain of a human MHC II β chain and transmembrane and cytoplasmic domains of a rodent MHC II β chain. In some aspects, a rodent portion of the chimeric MHC II complex is derived from a mouse H-2E protein, and a human portion is derived from a human HLA-DR4 protein. In some embodiments, the replacement of the endogenous MHC II loci described herein is made in a single ES cell, and the single ES cell is introduced into a rodent (e.g., mouse or rat) embryo to make a genetically modified rodent (e.g., mouse or rat).

Also provided herein are cells, e.g., isolated antigen-presenting cells, derived from the non-human animals (e.g., rodents, e.g., mice or rats) described herein. Tissues and embryos derived from the non-human animals described herein are also provided.

Any of the embodiments and aspects described herein can be used in conjunction with one another, unless otherwise indicated or apparent from the context. Other embodiments will become apparent to those skilled in the art from a review of the ensuing detailed description. The following detailed description includes exemplary representations of various embodiments of the invention, which are not restrictive of the invention as claimed. The accompanying figures constitute a part of this specification and, together with the description, serve only to illustrate embodiments and not to limit the invention.

DETAILED DESCRIPTION OF THE INVENTION

Definitions

Figure 1:
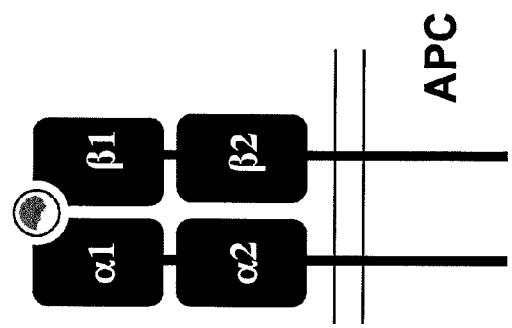
FIG. 1 is a schematic drawing of the MHC II class molecule expressed on the surface of an antigen presenting cell (APC), containing four domains: α1, α2, β1, and β2. The gray circle represents a peptide bound in the peptide-binding cleft.

The present invention provides genetically modified non-human animals (e.g., mice, rats, rabbits, etc.) that express human or humanized MHC II polypeptide; embryos, cells, and tissues comprising the same; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of MHC II to present a peptide of interest. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256:1443-45), hereby incorporated by reference. In some embodiments, the substitution is a moderately conservative substitution wherein the substitution has a nonnegative value in the PAM250 log-likelihood matrix.

Thus, also encompassed by the invention is a genetically modified non-human animal whose genome comprises a nucleotide sequence encoding a human or humanized MHC II polypeptide, wherein the polypeptide comprises conservative amino acid substitutions in the amino acid sequence described herein.

One skilled in the art would understand that in addition to the nucleic acid residues encoding a human or humanized MHC II polypeptide described herein, due to the degeneracy of the genetic code, other nucleic acids may encode the polypeptide of the invention. Therefore, in addition to a genetically modified non-human animal that comprises in its genome a nucleotide sequence encoding MHC II polypeptide with conservative amino acid substitutions, a non-human animal whose genome comprises a nucleotide sequence that differs from that described herein due to the degeneracy of the genetic code is also provided.

The term "identity" when used in connection with sequence includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments when comparing a chimeric human/non-human sequence to a human sequence, the human portion of the chimeric human/non-human sequence (but not the non-human portion) is used in making a comparison for the purpose of ascertaining a level of identity between a human sequence and a human portion of a chimeric human/non-human sequence (e.g., comparing a human ectodomain of a chimeric human/mouse protein to a human ectodomain of a human protein).

The terms "homology" or "homologous" in reference to sequences, e.g., nucleotide or amino acid sequences, means two sequences which, upon optimal alignment and comparison, are identical in at least about 75% of nucleotides or amino acids, at least about 80% of nucleotides or amino acids, at least about 90-95% nucleotides or amino acids, e.g., greater than 97% nucleotides or amino acids. One skilled in the art would understand that, for optimal gene targeting, the targeting construct should contain arms homologous to endogenous DNA sequences (i.e., "homology arms"); thus, homologous recombination can occur between the targeting construct and the targeted endogenous sequence.

The term "operably linked" refers to a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the chimeric or humanized protein of the invention may be operably linked to retain proper folding, processing, targeting, expression, and other functional properties of the protein in the cell. Unless stated otherwise, various domains of the chimeric or humanized protein of the invention are operably linked to each other.

The terms "MHC II complex," "MHC II protein," or the like, as used herein, include the complex between an MHC II α polypeptide and an MHC II β polypeptide. The term "MHC II α polypeptide" or "MHC II β polypeptide" (or the like), as used herein, includes the MHC I α polypeptide alone or MHC II β polypeptide alone, respectively. Similarly, the terms "HLA-DR4 complex", "HLA-DR4 protein," "H-2E complex," "H-2E" protein," or the like, refer to complex between α and β polypeptides. Typically, the terms "human MHC" and "HLA" are used interchangeably.

The term "replacement" in reference to gene replacement refers to placing exogenous genetic material at an endogenous genetic locus, thereby replacing all or a portion of the endogenous gene with an orthologous or homologous nucleic acid sequence. As demonstrated in the Examples below, nucleic acid sequence of endogenous MHC II locus was replaced by a nucleotide sequence comprising sequences encoding portions of human MHC II α and β polypeptides; specifically, encoding the extracellular portions of the MHC II α and β polypeptides.

"Functional" as used herein, e.g., in reference to a functional polypeptide, refers to a polypeptide that retains at least one biological activity normally associated with the native protein. For example, in some embodiments of the invention, a replacement at an endogenous locus (e.g., replacement at an endogenous non-human MHC II locus) results in a locus that fails to express a functional endogenous polypeptide.

Genetically Modified MHC II Animals

In various aspects, the invention generally provides genetically modified non-human animals that comprise in their genome a nucleotide sequence encoding a human or humanized MHC II complex; thus, the animals express a human or humanized MHC II complex (e.g., MHC II α and β polypeptides).

Figure 2:
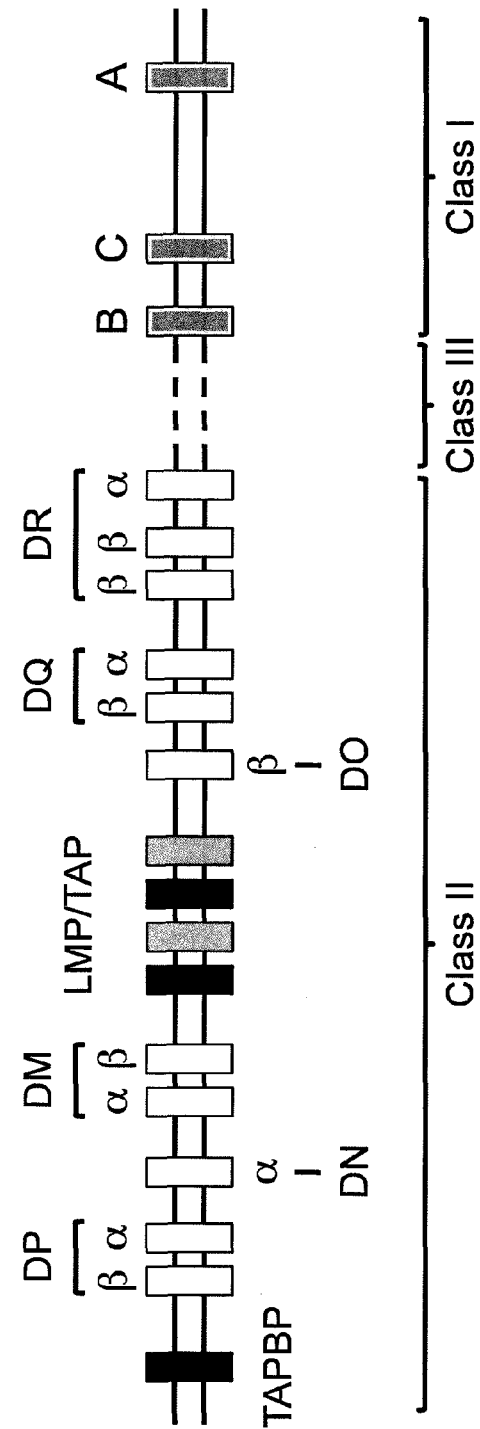
FIG. 2 is a schematic representation (not to scale) of the relative genomic structure of the human HLA, showing class I, II and III genes.
Figure 3:
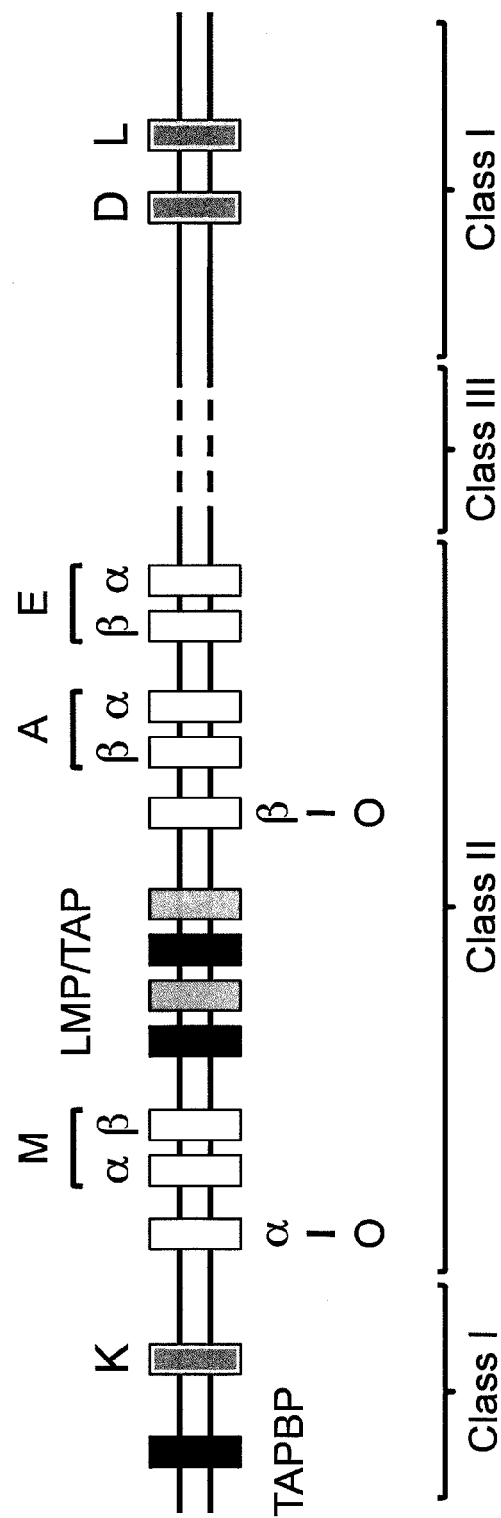
FIG. 3 is a schematic representation (not to scale) of the relative genomic structure of the mouse MHC, showing class I, II and III genes.

MHC genes are categorized into three classes: class I, class II, and class III, all of which are encoded either on human chromosome 6 or mouse chromosome 17. A schematic of the relative organization of the human and mouse MHC classes is presented in FIGS. 2 and 3, respectively. The majority of MHC genes are polymorphic, in fact they are the most polymorphic genes of the mouse and human genomes. MHC polymorphisms are presumed to be important in providing evolutionary advantage; changes in sequence can result in differences in peptide binding that allow for better antigen presentation. One exception is the human HLA-DRα chain and its mouse homolog, Eα (i.e., H-2Ea), which are monomorphic.

MHC class II complex comprises two non-covalently associated domains: an α chain and a β chain, also referred herein as an α polypeptide and a β polypeptide (FIG. 1). The protein spans the plasma membrane; thus it contains an extracellular domain, a transmembrane domain, and a cytoplasmic domain. The extracellular portion of the α chain includes α1 and α2 domains, and the extracellular portion of the β chain includes β1 and β2 domains. The α1 and β1 domains form a peptide-binding cleft on the cell surface. Due to the three-dimensional confirmation of the peptide-binding cleft of the MHC II complex, there is theoretically no upper limit on the length of the bound antigen, but typically peptides presented by MHC II are between 13 and 17 amino acids in length.

In addition to its interaction with the antigenic peptides, the peptide-binding cleft of the MHC II molecule interacts with invariant chain (Ii) during the processes of MHC II complex formation and peptide acquisition. The α/β MHC II dimers assemble in the endoplasmic reticulum and associate with Ii chain, which is responsible for control of peptide binding and targeting of the MHC II into endocytic pathway. In the endosome, Ii undergoes proteolysis, and a small fragment of Ii, Class II-associated invariant chain peptide (CLIP), remains at the peptide-binding cleft. In the endosome, under control of HLA-DM (in humans), CLIP is exchanged for antigenic peptides.

MHC II interacts with T cell co-receptor CD4 at the hydrophobic crevice at the junction between α2 and β2 domains. Wang and Reinherz (2002) Structural Basis of T Cell Recognition of Peptides Bound to MHC Molecules, Molecular Immunology, 38:1039-49. When CD4 and T cell receptor bind the same MHC II molecule complexed with a peptide, the sensitivity of a T cell to antigen is increased, and it requires 100-fold less antigen for activation. See, Janeway's Immunobiology, 7$^{th}$ Ed., Murphy et al. eds., Garland Science, 2008, incorporated herein by reference.

Numerous functions have been proposed for transmembrane and cytoplasmic domains of MHC II. In the case of cytoplasmic domain, it has been shown to be important for intracellular signaling, trafficking to the plasma membrane, and ultimately, antigen presentation. For example, it was shown that T cell hybridomas respond poorly to antigen-presenting cells (APCs) transfected with MHC II β chains truncated at the cytoplasmic domain, and induction of B cell differentiation is hampered. See, e.g., Smiley et al. (1996) Truncation of the class II β-chain cytoplasmic domain influences the level of class II/invariant chain-derived peptide complexes, Proc. Natl. Acad. Sci. USA, 93:241-44. Truncation of Class II molecules seems to impair cAMP production. It has been postulated that deletion of the cytoplasmic tail of MHC II affects intracellular trafficking, thus preventing the complex from coming across relevant antigens in the endocytic pathway. Smiley et al. (supra) demonstrated that truncation of class II molecules at the cytoplasmic domain reduces the number of CLIP/class II complexes, postulating that this affects the ability of CLIP to effectively regulate antigen presentation.

It has been hypothesized that, since MHC II clustering is important for T cell receptor (TCR) triggering, if MHC II molecules truncated at the cytoplasmic domain were prevented from binding cytoskeleton and thus aggregating, antigen presentation to T cells would be affected. Ostrand-Rosenberg et al. (1991) Abrogation of Tumorigenicity by MHC Class II Antigen Expression Requires the Cytoplasmic Domain of the Class II Molecule, J. Immunol. 147:2419-22. In fact, it was recently shown that HLA-DR truncated at the cytoplasmic domain failed to associate with the cytoskeleton following oligomerization. El Fakhy et al. (2004) Delineation of the HLA-DR Region and the Residues Involved in the Association with the Cytoskeleton, J. Biol. Chem. 279:18472-80. Importantly, actin cytoskeleton is a site of localized signal transduction activity, which can effect antigen presentation. In addition to association with cytoskeleton, recent studies have also shown that up to 20% of all HLA-DR molecules constitutively reside in the lipid rafts of APCs, which are microdomains rich in cholesterol and glycosphingolipids, and that such localization is important for antigen presentation, immune synapse formation, and MHC II-mediated signaling. See, e.g., Dolan et al. (2004) Invariant Chain and the MHC II Cytoplasmic Domains Regulate Localization of MHC Class II Molecules to Lipid Rafts in Tumor Cell-Based Vaccines, J. Immunol. 172:907-14. Dolan et al. suggested that truncation of cytoplasmic domain of MHC II reduces constitutive localization of MHC II to lipid rafts.

In addition, the cytoplasmic domain of MHC II, in particular the β chain, contains a leucine residue that is subject to ubiquitination by ubiquitin ligase, membrane-associated RING-CH I (MARCH I), which controls endocytic trafficking, internalization, and degradation of MHC II; and it has been shown that MARCH-mediated ubiquitination ceases upon dendritic cell maturation resulting in increased levels of MHC II at the plasma membrane. Shin et al. (2006) Surface expression of MHC class II in dendritic cells is controlled by regulated ubiquitination, Nature 444:115-18; De Gassart et al. (2008) MHC class II stabilization at the surface of human dendritic cells is the result of maturation-dependent MARCH I down-regulation, Proc. Natl. Acad. Sci. USA 105:3491-96.

Transmembrane domains of α and β chains of MHC II interact with each other and this interaction is important for proper assembly of class II MHC complex. Cosson and Bonifacino (1992) Role of Transmembrane Domain Interactions in the Assembly of Class II MHC Molecules, Nature 258:659-62. In fact, MHC II molecules in which the transmembrane domains of the α and β chains were replaced by the α chain of IL-2 receptor were retained in the ER and were barely detectable at the cell surface. Id. Through mutagenesis studies, conserved Gly residues at the α and β transmembrane domains were found to be responsible for MHC II assembly at the cell surface. Id. Thus, both transmembrane and cytoplasmic domains are crucial for the proper function of the MHC II complex.

In various embodiments, the invention provides a genetically modified non-human animal (e.g., mouse, rat, rabbit, etc.) that comprises in its genome a nucleotide sequence encoding a human or humanized MHC II complex, e.g., a human or humanized MHC II α and/or β polypeptide(s). The non-human animal may comprise in its genome a nucleotide sequence that encodes an MHC II complex that is partially human and partially non-human, e.g., a non-human animal that expresses a chimeric human/non-human MHC II complex (e.g., a non-human animal that expresses chimeric human/non-human MHC II α and β polypeptides). In one aspect, the non-human animal only expresses the human or humanized MHC II complex, e.g., a chimeric human/non-human MHC II complex, and does not express an endogenous non-human MHC II complex from an endogenous MHC II locus. In some embodiments, the animal is incapable of expressing any endogenous non-human MHC II complex from an endogenous MHC II locus, but only expresses the human or humanized MHC II complex. In various embodiments, the genetically modified non-human animal (e.g., mouse, rat, rabbit, etc.) comprises in its germline a nucleotide sequence encoding a human or humanized MHC II complex, e.g., a human or humanized MHC II α and/or β polypeptide(s).

In one aspect, a chimeric human/non-human MHC II complex is provided. In one embodiment, the chimeric human/non-human MHC II complex comprises a chimeric human/non-human MHC II α polypeptide and a chimeric human/non-human MHC II β polypeptide. In one aspect, a human portion of the chimeric MHC II α polypeptide and/or a human portion of the chimeric MHC II β polypeptide comprises a peptide-binding domain of a human MHC II α polypeptide and/or human MHC II β polypeptide, respectively. In one aspect, a human portion of the chimeric MHC II α and/or β polypeptide comprises an extracellular domain of a human MHC II α and/or β polypeptide, respectively. In one embodiment, a human portion of the chimeric MHC II α polypeptide comprises a1 domain of a human MHC II α polypeptide; in another embodiment, a human portion of the chimeric MHC II α polypeptide comprises α1 and α2 domains of a human MHC II α polypeptide. In an additional embodiment, a human portion of the chimeric MHC II polypeptide comprises β1 domain of a human MHC II β polypeptide; in another embodiment, a human portion of the chimeric MHC II β polypeptide comprises β1 and β2 domains of a human MHC II β polypeptide.

The human portion of the MHC II α and β polypeptides described herein may be encoded by any of HLA-DP, -DQ, and -DR loci. A list of commonly used HLA antigens and alleles is described in Shankarkumar et al. ((2004) The Human Leukocyte Antigen (HLA) System, Int. J. Hum. Genet. 4(2):91-103), incorporated herein by reference. Shankarkumar et al. also present a brief explanation of HLA nomenclature used in the art. Additional information regarding HLA nomenclature and various HLA alleles can be found in Holdsworth et al. (2009) The HLA dictionary 2008: a summary of HLA-A, -B, -C, -DRB1/3/4/5, and DQB1 alleles and their association with serologically defined HLA-A, -B, -C, -DR, and -DQ antigens, Tissue Antigens 73:95-170, and a recent update by Marsh et al. (2010) Nomenclature for factors of the HLA system, 2010, Tissue Antigens 75:291-455, both incorporated herein by reference. Thus, the human or humanized MHC II polypeptide may be derived from any functional human HLA molecules described therein.

In one specific aspect, the human portions of the humanized MHC II complex described herein are derived from human HLA-DR, e.g., HLA-DR4. Typically, HLA-DR α chains are monomorphic, e.g., the α chain of HLA-DR complex is encoded by HLA-DRA gene (e.g., HLA-DRα*01 gene). On the other hand, the HLA-DR β chain is polymorphic. Thus, HLA-DR4 comprises an α chain encoded by HLA-DRA gene and a β chain encoded by HLA-DRB1 gene (e.g., HLA-DRβ1*04 gene). As described herein below, HLA-DR4 is known to be associated with incidence of a number of autoimmune diseases, e.g., rheumatoid arthritis, type I diabetes, multiple sclerosis, etc. In one embodiment of the invention, the HLA-DRA allele is HLA-DRα*01 allele, e.g., HLA-DRα*01:01:01:01. In another embodiment, the HLA-DRB allele is HLA-DRβ1*04, e.g., HLA-DRβ1*04:01:01. Although the present Examples describe these particular HLA sequences; any suitable HLA-DR sequences are encompassed herein, e.g., polymorphic variants exhibited in human population, sequences with one or more conservative or non-conservative amino acid modifications, nucleic acid sequences differing from the sequences described herein due to the degeneracy of genetic code, etc.

The human portions of the humanized MHC II complex may be encoded by nucleotide sequences of HLA alleles known to be associated with common human diseases. Such HLA alleles include, but are not limited to, HLA-DRB1*0401, -DRB1*0301, -DQA1*0501, -DQB1*0201, -DRB1*1501, -DRB1*1502, -DQB1*0602, -DQA1*0102, -DQA1*0201, -DQB1*0202, -DQA1*0501, and combinations thereof. For a summary of HLA allele/disease associations, see Bakker et al. (2006) A high-resolution HLA and SNP haplotype map for disease association studies in the extended human MHC, Nature Genetics 38:1166-72 and Supplementary Information, incorporated herein by reference.

In one aspect, a non-human portion of the chimeric human/non-human MHC II complex comprises transmembrane and/or cytoplasmic domains of an endogenous non-human (e.g., rodent, e.g., mouse, rat, etc.) MHC II complex. Thus, a non-human portion of the chimeric human/non-human MHC II α polypeptide may comprise transmembrane and/or cytoplasmic domains of an endogenous non-human MHC II α polypeptide. A non-human portion of the chimeric human/non-human MHC II β polypeptide may comprise transmembrane and/or cytoplasmic domains of an endogenous non-human MHC polypeptide. In one aspect, the animal is a mouse, and non-human portions of the chimeric α and β polypeptides are derived from a mouse H-2E protein. Thus, non-human portions of the chimeric α and β polypeptides may comprise transmembrane and cytoplasmic domains derived from a mouse H-2E protein. Although specific H-2E sequences are contemplated in the Examples, any suitable sequences, e.g., polymorphic variants, conservative/non-conservative amino acid substitutions, etc., are encompassed herein.

In various aspects of the invention, the sequence(s) encoding a chimeric human/non-human MHC II complex are located at an endogenous non-human MHC II locus (e.g., mouse H-2A and/or H-2E locus). In one embodiment, this results in a replacement of an endogenous MHC II gene(s) or a portion thereof with a nucleotide sequence(s) encoding a human or humanized MHC II protein, e.g., a chimeric gene encoding a chimeric human/non-human MHC II protein described herein. Since the nucleotide sequences encoding MHC II α and β polypeptides are located in proximity to one another on the chromosome, a replacement can be designed to target the two genes either independently or together; both of these possibilities are encompassed herein. In one embodiment, the replacement comprises a replacement of an endogenous nucleotide sequence encoding an MHC II α and β polypeptides with a nucleotide sequence encoding a chimeric human/non-human MHC a polypeptide and a chimeric human/non-human MHC β polypeptide. In one aspect, the replacement comprises replacing nucleotide sequences representing one or more (e.g., two) endogenous MHC II genes. Thus, the non-human animal contains a chimeric human/non-human nucleotide sequence at an endogenous MHC II locus, and expresses a chimeric human/non-human MHC II protein from the endogenous non-human locus.

Thus, provided herein is a non-human animal comprising at an endogenous MHC II gene locus a first nucleotide sequence encoding a chimeric human/non-human MHC II α polypeptide and a second nucleotide sequence encoding a chimeric human/non-human MHC II β polypeptide, wherein a human portion of the chimeric human/non-human MHC II α polypeptide comprises a human MHC II α extracellular domain and a human portion of the chimeric human/non-human MHC II β polypeptide comprises a human MHC II β extracellular domain, and wherein the chimeric human/non-human MHC II α and MHC II β polypeptides form a functional MHC II complex on a surface of a cell.

A chimeric human/non-human polypeptide may be such that it comprises a human or a non-human leader (signal) sequence. In one embodiment, the chimeric MHC II α polypeptide comprises a non-human leader sequence of an endogenous MHC II α polypeptide. In one embodiment, the chimeric MHC II β polypeptide comprises a non-human leader sequence of an endogenous MHC II β polypeptide. In an alternative embodiment, the chimeric MHC II α and/or MHC II β polypeptide comprises a non-human leader sequence of MHC II α and/or MHC II β polypeptide, respectively, from another non-human animal, e.g., another rodent or another mouse strain. Thus, the nucleotide sequence encoding the chimeric MHC II α and/or MHC II β polypeptide may be operably linked to a nucleotide sequence encoding a non-human MHC II α and/or MHC II β leader sequence, respectively. In yet another embodiment, the chimeric MHC II α and/or MHC II β polypeptide comprises a human leader sequence of human MHC II α and/or human MHC II β polypeptide, respectively (e.g., a leader sequence of human HLA-DRA and/or human HLA-DRβ1*04, respectively).

A chimeric human/non-human MHC II α and/or MHC II β polypeptide may comprise in its human portion a complete or substantially complete extracellular domain of a human MHC II α and/or human MHC II β polypeptide, respectively. Thus, a human portion may comprise at least 80%, preferably at least 85%, more preferably at least 90%, e.g., 95% or more of the amino acids encoding an extracellular domain of a human MHC II α and/or human MHC II β polypeptide (e.g., human HLA-DRA and/or human HLA-DRβ1*04). In one example, substantially complete extracellular domain of the human MHC II α and/or human MHC II β polypeptide lacks a human leader sequence. In another example, the chimeric human/non-human MHC II α and/or the chimeric human/non-human MHC II β polypeptide comprises a human leader sequence.

Moreover, the chimeric MHC II α and/or MHC II β polypeptide may be expressed under the control of endogenous non-human promoter and regulatory elements, e.g., mouse MHC II α and/or MHC II β regulatory elements, respectively. Such arrangement will facilitate proper expression of the chimeric MHC II polypeptides in the non-human animal, e.g., during immune response in the non-human animal.

The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the invention relates to a genetically modified mouse that comprises in its genome a nucleotide sequence encoding a chimeric human/mouse MHC II complex, e.g., chimeric human/mouse MHC II α and β polypeptides. In one embodiment, a human portion of the chimeric human/mouse MHC II α polypeptide comprises a human MHC II α peptide binding or extracellular domain and a human portion of the chimeric human/mouse MHC II β polypeptide comprises a human MHC II β peptide binding or extracellular domain. In some embodiments, the mouse does not express a peptide binding or an extracellular domain of endogenous mouse α and/or β polypeptide from an endogenous mouse locus (e.g., H-2A and/or H-2E locus). In some embodiments, the mouse comprises a genome that lacks a gene that encodes a functional MHC class II molecule comprising an H-2Ab1, H-2Aa, H-2Eb1, H-2Eb2, H-2Ea, and a combination thereof. The peptide-binding domain of the human MHC II α polypeptide may comprise α1 domain and the peptide-binding domain of the human MHC II β polypeptide may comprise a β1 domain; thus, the peptide-binding domain of the chimeric MHC II complex may comprise human α1 and β1 domains. The extracellular domain of the human MHC II α polypeptide may comprise α1 and α2 domains and the extracellular domain of the human MHC II polypeptide may comprise β1 and β2 domains; thus, the extracellular domain of the chimeric MHC II complex may comprise human α1, α2, β1 and β2 domains. In one embodiment, the mouse portion of the chimeric MHC II complex comprises transmembrane and cytosolic domains of mouse MHC II, e.g. mouse H-2E (e.g., transmembrane and cytosolic domains of mouse H-2E α and β chains).

Therefore, in one embodiment, a genetically modified mouse is provided, wherein the mouse comprises at an endogenous mouse MHC II locus a first nucleotide sequence encoding a chimeric human/mouse MHC II α polypeptide and a second nucleotide sequence encoding a chimeric human/mouse MHC II β polypeptide, wherein a human portion of the chimeric MHC II α polypeptide comprises an extracellular domain derived from an α polypeptide of a human HLA-DR4 protein and the human portion of the chimeric MHC II β polypeptide comprises an extracellular domain derived from a β polypeptide of a human HLA-DR4 protein, wherein a mouse portion of the chimeric MHC II α polypeptide comprises transmembrane and cytoplasmic domains of a mouse H-2E α chain and a mouse portion of the chimeric MHC II β polypeptide comprises transmembrane and cytoplasmic domains of a mouse H-2E β chain, and wherein the mouse expresses a functional chimeric HLA-DR4/H-2E MHC II complex. In one embodiment the chimeric HLA-DR4/H-2E MHC II complex comprises an MHC II α chain that includes extracellular domains (e.g., α1, and α2 domains) derived from HLA-DR4 protein (HLA-DRA α1, and α2 domains) and transmembrane and cytoplasmic domains from a mouse H-2E α chain, as well as an MHC II β chain that includes extracellular domains (e.g., β1 and β2 domains) derived from HLA-DR4 (HLA-DRβ1*04 β1 and β2 domains) and transmembrane and cytoplasmic domains from mouse H-2E β chain. In one aspect, the mouse does not express functional endogenous H-2A and H-2E polypeptides from their endogenous mouse loci (e.g., the mouse does not express H-2Ab1, H-2Aa, H-2Eb1, H-2Eb2, and H-2Ea polypeptides). In various embodiments, expression of the first and second nucleotide sequences is under the control of respective endogenous mouse promoters and regulatory elements. In various embodiments of the invention, the first and the second nucleotide sequences are located on the same chromosome. In some aspects, the mouse comprises two copies of the chimeric MHC II locus containing the first and the second nucleotide sequences, while in other aspects, the mouse comprises one copy of the MHC II locus containing the first and the second nucleotide sequences. Thus, the mouse may be homozygous or heterozygous for the chimeric MHC II locus containing the first and the second nucleotide sequences. In various embodiments, the first and the second nucleotide sequences are comprises in the germline of the mouse.

In some embodiments described herein, a mouse is provided that comprises a chimeric MHC II locus at an endogenous mouse MHC II locus, e.g., via replacement of endogenous mouse H-2A and H-2E genes. In some aspects, the chimeric locus comprises a nucleotide sequence that encodes an extracellular domain of a human HLA-DRA and transmembrane and cytoplasmic domains of a mouse H-2E α chain, as well as an extracellular domain of a human HLA-DRβ1*04 and transmembrane and cytoplasmic domains of a mouse H-2E β chain. The various domains of the chimeric locus are linked in such a fashion that the locus expresses a functional chimeric human/mouse MHC II complex.

In various embodiments, a non-human animal (e.g., a rodent, e.g., a mouse or rat) that expresses a functional chimeric MHC II protein from a chimeric MHC II locus as described herein displays the chimeric protein on a cell surface. In one embodiment, the non-human animal expresses the chimeric MHC II protein on a cell surface in a cellular distribution that is the same as observed in a human. In one aspect, the cell displays a peptide fragment (antigen fragment) bound to an extracellular portion (e.g., human HLA-DR4 extracellular portion) of the chimeric MHC II protein.

In various embodiments, a cell displaying the chimeric MHC II protein, e.g., HLA-DR4/H-2E protein, is an antigen-presenting cell (APC) e.g., a macrophage, a dendritic cell, or a B cell. In some embodiments, the peptide fragment presented by the chimeric protein is derived from a tumor. In other embodiments, the peptide fragment presented by the chimeric MHC II protein is derived from a pathogen, e.g., a bacterium, a virus, or a parasite.

The chimeric MHC II protein described herein may interact with other proteins on the surface of the same cell or a second cell. In some embodiments, the chimeric MHC II protein interacts with endogenous non-human proteins on the surface of said cell. The chimeric MHC II protein may also interact with human or humanized proteins on the surface of the same cell or a second cell. In some embodiments, the second cell is a T cell, and the chimeric MHC II protein interacts with T cell receptor (TCR) and its co-receptor CD4. In some embodiments, the T cell is an endogenous mouse T cell. In other embodiments, the T cell is a human T cell. In some embodiments, the TCR is a human or humanized TCR. In additional embodiments, the CD4 is a human or humanized CD4. In other embodiment, either one or both of TCR and CD4 are non-human, e.g., mouse or rat.

In one embodiment, a genetically modified non-human animal as described herein is provided that does not develop tumors at a higher rate than a wild-type animal that lacks a chimeric MHC II gene. In some embodiments, the animal does not develop hematological malignancies, e.g., various T and B cell lymphomas, leukemias, composite lymphomas (e.g., Hodgkin's lymphoma), at a higher rate than the wild-type animal.

In addition to a genetically engineered non-human animal, a non-human embryo (e.g., a rodent, e.g., a mouse or a rat embryo) is also provided, wherein the embryo comprises a donor ES cell that is derived from a non-human animal (e.g., a rodent, e.g., a mouse or a rat) as described herein. In one aspect, the embryo comprises an ES donor cell that comprises the chimeric MHC II gene, and host embryo cells.

Also provided is a tissue, wherein the tissue is derived from a non-human animal (e.g., a rodent, e.g., a mouse or a rat) as described herein, and expresses the chimeric MHC II protein (e.g., HLA-DR4/H-2E protein).

In addition, a non-human cell isolated from a non-human animal as described herein is provided. In one embodiment, the cell is an ES cell. In one embodiment, the cell is an antigen-presenting cell, e.g., dendritic cell, macrophage, B cell. In one embodiment, the cell is an immune cell. In one embodiment, the immune cell is a lymphocyte.

Also provided is a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a non-human induced pluripotent cell comprising gene encoding a chimeric MHC II protein (e.g., HLA-DR4/H-2E protein) as described herein is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

In one aspect, an in vitro preparation is provided that comprises a first cell that bears a chimeric human/rodent MHC II surface protein that comprises a bound peptide to form a chimeric human/rodent MHC II/peptide complex, and a second cell that binds the chimeric human/rodent MHC II/peptide complex. In one embodiment, the second cell comprises a human or humanized T-cell receptor, and in one embodiment further comprises a human or humanized CD4. In one embodiment, the second cell is a rodent (e.g., mouse or rat) cell comprising a human or humanized T-cell receptor and a human or humanized CD4 protein. In embodiment, the second cell is a human cell.

Also provided is a method for making a genetically engineered non-human animal (e.g., a genetically engineered rodent, e.g., a mouse or rat) described herein. The method for making a genetically engineered non-human animal results in the animal whose genome comprises a nucleotide sequence encoding a chimeric MHC II protein (e.g., chimeric MHC II α and β polypeptides). In one embodiment, the method results in a genetically engineered mouse, whose genome comprises at an endogenous MHC II locus a nucleotide sequence encoding a chimeric human/mouse MHC II protein, wherein a human portion of the chimeric MHC II protein comprises an extracellular domain of a human HLA-DR4 and a mouse portion comprises transmembrane and cytoplasmic domains of a mouse H-2E. In some embodiments, the method utilizes a targeting construct made using VELOCIGENE® technology, introducing the construct into ES cells, and introducing targeted ES cell clones into a mouse embryo using VELOCIMOUSE® technology, as described in the Examples. In one embodiment, the ES cells are a mix of 129 and C57BL/6 mouse strains; in one embodiment, the ES cells are a mix of BALB/c and 129 mouse strains.

A nucleotide construct used for generating genetically engineered non-human animals described herein is also provided. In one aspect, the nucleotide construct comprises: 5' and 3' non-human homology arms, a DNA fragment comprising human HLA-DR α and β chain sequences, and a selection cassette flanked by recombination sites. In one embodiment, the human HLA-DR α and β chain sequences are genomic sequences that comprise introns and exons of human HLA-DR α and β chain genes. In one embodiment, the non-human homology arms are homologous to non-human MHC II genomic sequence.

In one embodiment, the human HLA-DR α chain sequence comprises an α1 and α2 domain coding sequence. In a specific embodiment, it comprises, from 5' to 3': α1 exon (exon 2), α1/α2 intron (intron 2), and α2 exon (exon 3). In one embodiment, the human HLA-DR β chain sequence comprises a β1 and β2 domain coding sequence. In a specific embodiment, it comprises, from 5' to 3': β1 exon (exon 2), β1/β2 intron (intron 2), and β2 exon (exon 3).

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, SPEC, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art. A selection cassette may be located anywhere in the construct outside the coding region. In one embodiment, the selection cassette is located in the β chain intron, e.g., β2/transmembrane domain intron (intron 3).

In one embodiment, 5' and 3' homology arms comprise genomic sequence at 5' and 3' locations of endogenous non-human MHC II locus. In one embodiment, the 5' homology arm comprises genomic sequence upstream of mouse H-2Ab1 gene and the 3' homology arm comprises genomic sequence downstream of mouse H-2Ea gene. In this embodiment, the construct allows replacement of both mouse H-2E and H-2A genes.

Figure 5:
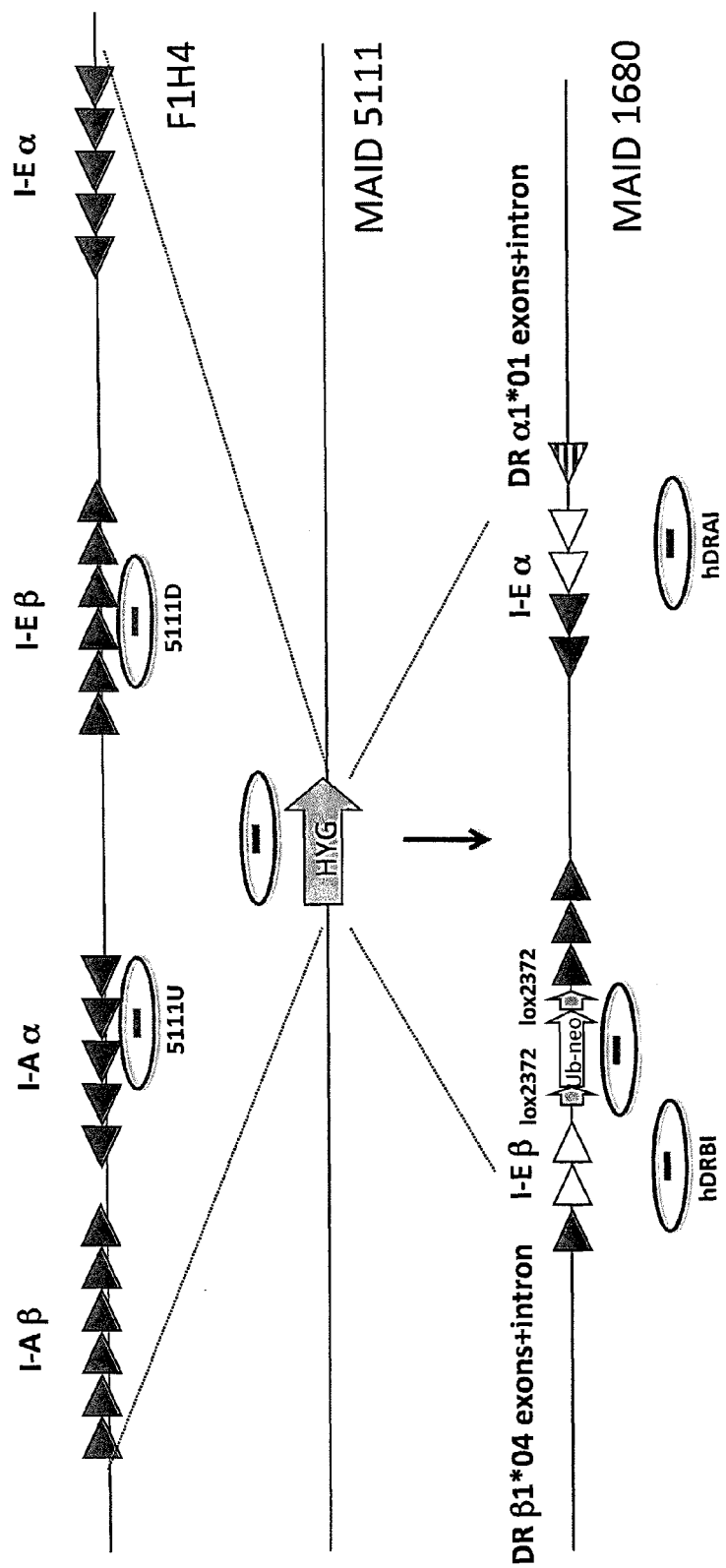
FIG. 5 shows a schematic illustration, not to scale, of MHC class II I-E and I-A genes, showing knockout of the mouse locus using a hygromycin cassette, followed by introduction of a vector comprising a humanized I-E β and I-E α (i.e., H-2Eβ/HLA-DRβ1*04 and H-2Eα/HLA-DRα*01 chimera, respectively). Open triangles represent human exons; filled triangles represent mouse exons. Probes used for genotyping are encircled.

Thus, in one aspect, a nucleotide construct is provided comprising, from 5' to 3': a 5' homology arm containing mouse genomic sequence upstream of mouse H-2Ab1 gene, a first nucleotide sequence comprising a sequence encoding a chimeric human/mouse MHC II β chain, a second nucleotide sequence comprising a sequence encoding a chimeric human/mouse MHC II α chain, and a 3' homology arm containing mouse genomic sequence downstream of mouse H-2Ea gene. In a specific embodiment, the first nucleotide sequence comprising a sequence encoding a chimeric human/mouse MHC chain comprises human β1 exon, β1/β2 intron, β2 exon, an a selection cassette flanked by recombination sites inserted in the intronic region between the human β2 exon sequence and the sequence of a mouse transmembrane domain exon. In a specific embodiment, the second nucleotide sequence comprising a sequence encoding a chimeric human/mouse MHC II α chain comprises human α1 exon, α1/α2 intron, and human α2 exon. An exemplary construct of the invention is depicted in FIG. 5 (MAID 1680).

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCT (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

The disclosure also provides a method of modifying an MHC II locus of a non-human animal to express a chimeric human/non-human MHC II complex described herein. In one embodiment, the invention provides a method of modifying an MHC II locus of a mouse to express a chimeric human/mouse MHC II complex comprising replacing at the endogenous mouse MHC II locus a nucleotide sequence encoding a mouse MHC II complex with a nucleotide sequence encoding a chimeric human/mouse MHC II complex. In a specific aspect, the nucleotide sequence encoding the chimeric human/mouse MHC II complex comprises a first nucleotide sequences encoding an extracellular domain of a human MHC II α chain (e.g., HLA-DR4 α chain) and transmembrane and cytoplasmic domains of a mouse MHC II α chain (e.g., H-2E α chain) and a second nucleotide sequence encoding an extracellular domain of a human MHC II β chain (e.g., HLA-DR4 β chain) and transmembrane and cytoplasmic domains of a mouse MHC II β chain (e.g., H-2E β chain, e.g., H-2Eb1 chain). In some embodiments, the modified mouse MHC II locus expresses a chimeric HLA-DR4/H-2E protein.

In one aspect, a method for making a chimeric human HLA class II/non-human MHC class II molecule is provided, comprising expressing in a single cell a chimeric HLA-DR4/H-2E protein from a nucleotide construct as described herein. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric HLA-DR4/H-2E protein is provided. In one embodiment, the cell comprises an expression vector comprising a chimeric MHC class II sequence as described herein. In one embodiment, the cell is selected from CHO, COS, 293, HeLa, and a retinal cell expressing a viral nucleic acid sequence (e.g., a PERC.6™ cell).

A chimeric MHC class II molecule made by a non-human animal as described herein is also provided, wherein the chimeric MHC class II molecule comprises α1, α2, β1, and β2 domains from a human MHC II protein, e.g., HLA-DR4 protein, and transmembrane and cytoplasmic domains from a non-human MHC II protein, e.g., mouse H-2E protein. The chimeric MHC II complex comprising an extracellular domain of HLA-DR4 described herein maybe detected by anti-HLA-DR antibodies. Thus, a cell displaying chimeric human/non-human MHC II polypeptide may be detected and/or selected using anti-HLA-DR antibody.

Although the Examples that follow describe a genetically engineered animal whose genome comprises a replacement of a nucleotide sequence encoding mouse H-2A and H-2E proteins with a nucleotide sequence encoding a chimeric human/mouse HLA-DR4/H-2E protein, one skilled in the art would understand that a similar strategy may be used to introduce chimeras comprising other human MHC II genes (HLA-DP and HLA-DQ). Thus, an additional embodiment of the invention is directed to a genetically engineered animal whose genome comprises a nucleotide sequence encoding a chimeric HLA-DQ/H-2A protein. In one embodiment, the nucleotide sequence encodes a chimeric HLA-DQ2.5/H-2A protein. In another embodiment, the nucleotide sequence encodes a chimeric HLA-DQ8/H-2A protein. In addition, introduction of multiple humanized MHC II molecules (e.g., chimeric HLA-DR/H-2E and HLA-DQ/H-2A) is also contemplated.

Use of Genetically Modified Animals

In various embodiments, the genetically modified non-human animals described herein make APCs with human or humanized MHC II on the cell surface and, as a result, present peptides derived from cytosolic proteins as epitopes for T cells in a human-like manner, because substantially all of the components of the complex are human or humanized. The genetically modified non-human animals of the invention can be used to study the function of a human immune system in the humanized animal; for identification of antigens and antigen epitopes that elicit immune response (e.g., T cell epitopes, e.g., unique human cancer epitopes), e.g., for use in vaccine development; for evaluation of vaccine candidates and other vaccine strategies; for studying human autoimmunity; for studying human infectious diseases; and otherwise for devising better therapeutic strategies based on human MHC expression.

MHC II complex binds peptides derived from extracellular proteins, e.g., extracellular bacterium, neighboring cells, or polypeptides bound by B cell receptors and internalized into a B cell. Once extracellular proteins enter endocytic pathway, they are degraded into peptides, and peptides are bound and presented by MHC II. Once a peptide presented by MHC II is recognized by CD4+ T cells, T cells are activated, proliferate, differentiate to various T helper subtypes (e.g., $T_H1$, $T_H2$), and lead to a number of events including activation of macrophage-mediated pathogen killing, B cell proliferation, and antibody production. Because of MHC II role in immune response, understanding of MHC II peptide presentation is important in the development of treatment for human pathologies. However, presentation of antigens in the context of mouse MHC II is only somewhat relevant to human disease, since human and mouse MHC complexes recognize antigens differently, e.g., a mouse MHC II may not recognize the same antigens or may present different epitopes than a human MHC II. Thus, the most relevant data for human pathologies is obtained through studying the presentation of antigen epitopes by human MHC II.

Thus, in various embodiments, the genetically engineered animals of the present invention are useful, among other things, for evaluating the capacity of an antigen to initiate an immune response in a human, and for generating a diversity of antigens and identifying a specific antigen that may be used in human vaccine development.

In one aspect, a method for determining antigenicity in a human of a peptide sequence is provided, comprising exposing a genetically modified non-human animal as described herein to a molecule comprising the peptide sequence, allowing the non-human animal to mount an immune response, and detecting in the non-human animal a cell that binds a sequence of the peptide presented by a humanized MHC II complex described herein.

In one aspect, a method for determining whether a peptide will provoke an immune response in a human is provided, comprising exposing a genetically modified non-human animal as described herein to the peptide, allowing the non-human animal to mount an immune response, and detecting in the non-human animal a cell that binds a sequence of the peptide by a chimeric human/non-human MHC class II molecule as described herein. In one embodiment, the non-human animal following exposure comprises an MHC class II-restricted CD4+ T cell that binds the peptide.

In one aspect, a method for identifying a human CD4+ T cell epitope is provided, comprising exposing a non-human animal as described herein to an antigen comprising a putative T cell epitope, allowing the non-human animal to mount an immune response, and identifying the epitope bound by the MHC class II-restricted CD4+ T cell.

In one aspect, a method is provided for identifying an antigen that generates a CD4+ T cell response in a human, comprising exposing a putative antigen to a mouse as described herein, allowing the mouse to generate an immune response, detecting a CD4+ T cell response that is specific for the antigen in the context of a human MHC II molecule (e.g., an HLA-DR molecule), and identifying the antigen bound by the human MHC II-restricted molecule (e.g., human HLA-DR restricted molecule).

In one embodiment, the antigen comprises a bacterial protein. In one embodiment, the antigen comprises a human tumor cell antigen. In one embodiment, the antigen comprises a putative vaccine for use in a human, or another biopharmaceutical. In one embodiment, the antigen comprises a human epitope that generates antibodies in a human. In yet another embodiment, an antigen comprises a yeast or fungal cell antigen. In yet another embodiment, an antigen is derived from a human parasite.

In one aspect, a method is provided for determining whether a putative antigen contains an epitope that upon exposure to a human immune system will generate an HLA-DR-restricted immune response (e.g., HLA-DR4-restricted response), comprising exposing a mouse as described herein to the putative antigen and measuring an antigen-specific HLA-DR-restricted (e.g., HLA-DR4-restricted) immune response in the mouse. In another aspect, a method is provided for determining wherein a putative antigen contains an epitope that upon exposure to a human immune system will generate an HLA-DQ-restricted response.

Also provided is a method of generating antibodies to an antigen, e.g., an antigen derived from bacterium, parasite, etc., presented in the context of a human MHC II complex, comprising exposing a mouse described herein to an antigen, allowing a mouse to mount an immune response, wherein the immune response comprises antibody production, and isolating an antibody that recognizes the antigen presented in the context of human MHC II complex. In one embodiment, in order to generate antibodies to the peptide-MHC II, the MHC II humanized mouse is immunized with a peptide-MHC II immunogen.

In one aspect, a method for identifying a T cell receptor variable domain that recognizes an antigen presented in the context of MHC II (e.g., human tumor antigen, a vaccine, etc.) is provided, comprising exposing a mouse comprising a humanized MHC II complex described herein to the antigen, allowing the mouse to generate an immune response, and isolating from the mouse a nucleic acid sequence encoding a variable domain of a T cell receptor that binds MHC II-restricted antigen. In one embodiment, the antigen is presented in the context of a humanized MHC II (e.g., human HLA II ectodomain/mouse MHC II transmembrane and/or cytoplasmic domain).

The consequence of interaction between a T cell and an APC displaying a peptide in the context of MHC II (e.g., human HLA II ectodomain/mouse MHC II transmembrane and/or cytoplasmic domain) can be measured by a number of techniques known in the art, e.g., T cell proliferation assays, cytokine release assays, etc.

In addition to the ability to identify antigens and their T cell epitopes from pathogens or neoplasms, the genetically modified animals of the invention can be used to identify autoantigens of relevance to human autoimmune disease, and otherwise study human autoimmune disease progression. It is known that polymorphisms within the HLA loci play a role in predisposition to human autoimmune disease. In fact, specific polymorphisms in HLA-DR and HLA-DQ loci have been identified that correlate with development of rheumatoid arthritis, type I diabetes, Hashimoto's thyroiditis, multiple sclerosis, myasthenia gravis, Graves' disease, systemic lupus erythematosus, celiac disease, Crohn's disease, ulcerative colitis, and other autoimmune disorders. See, e.g., Wong and Wen (2004) What can the HLA transgenic mouse tell us about autoimmune diabetes?, Diabetologia 47:1476-87; Taneja and David (1998) HLA Transgenic Mice as Humanized Mouse Models of Disease and Immunity, J. Clin. Invest. 101:921-26; Bakker et al. (2006), supra; and International MHC and Autoimmunity Genetics Network (2009) Mapping of multiple susceptibility variants within the MHC region for 7 immune-mediated diseases, Proc. Natl. Acad. Sci. USA 106: 18680-85.

Thus, the methods of making a humanized MHC II complex animals described herein can be used to introduce MHC II molecules thought to be associated with specific human autoimmune diseases, and progression of human autoimmune disease can be studied. In addition, non-human animals described herein can be used to develop animal models of human autoimmune disease. Mice according to the invention carrying humanized MHC II proteins described herein can be used to identify potential autoantigens, to map epitopes involved in disease progression, and to design strategies for autoimmune disease modulation.

In addition, the genetically modified animals described herein may be used in the study of human allergic response. As allergic responses appear to be associated with MHC II alleles, genetically modified animals described herein may be used to determine HLA restriction of allergen specific T cell response and to develop strategies to combat allergic response.

EXAMPLES

The invention will be further illustrated by the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1

Deletion of the Endogenous MHC Class II H-2A and H-2E Loci

The targeting vector for introducing a deletion of the endogenous MHC class II H-2Ab1, H-2Aa, H-2Eb1, H-2Eb2, and H-2Ea genes was made using VELOCIGENE® genetic engineering technology (see, e.g., U.S. Pat. No. 6,586,251 and Valenzuela et al., supra). Bacterial Artificial Chromosome (BAC) RP23-458i22 (Invitrogen) DNA was modified to delete the endogenous MHC class II genes H-2Ab1, H-2Aa, H-2Eb1, H-2Eb2, and H-2Ea.

Briefly, upstream and downstream homology arms were derived by PCR of mouse BAC DNA from locations 5' of the H-2Ab1 gene and 3' of the H-2Ea gene, respectively. As depicted in FIG. 5, these homology arms were used to make a cassette that deleted ~79 kb of RP23-458i22 comprising genes H-2Ab1, H-2Aa, H-2Eb1, H-2Eb2, and H-2Ea of the MHC class II locus by bacterial homologous recombination (BHR). This region was replaced with a hygromycin cassette flanked by lox66 and lox71 sites. The final targeting vector from 5' to 3' included a 34 kb homology arm comprising mouse genomic sequence 5' to the H-2Ab1 gene of the endogenous MHC class II locus, a 5' lox66 site, a hygromycin cassette, a 3' lox71 site and a 63 kb homology arm comprising mouse genomic sequence 3' to the H-2Ea gene of the endogenous MHC class II locus (MAID 5111, see FIG. 5).

The BAC DNA targeting vector (described above) was used to electroporate mouse ES cells to create modified ES cells comprising a deletion of the endogenous MHC class II locus. Positive ES cells containing a deleted endogenous MHC class II locus were identified by the quantitative PCR assay using TAQMAN™ probes (Lie and Petropoulos (1998) Curr. Opin. Biotechnology 9:43-48). The upstream region of the deleted locus was confirmed by PCR using primers 5111U F (CAGAACGCCAGGCTGTAAC; SEQ ID NO:1) and 5111U R (GGAGAGCAGGGTCAGTCAAC; SEQ ID NO:2) and probe 5111U P (CACCGCCACTCACAGCTC-CTTACA; SEQ ID NO:3), whereas the downstream region of the deleted locus was confirmed using primers 5111 D F (GTGGGCACCATCTTCATCATTC; SEQ ID NO:4) and 5111 D R (CTTCCTTTCCAGGGTGTGACTC; SEQ ID NO:5) and probe 5111 D P (AGGCCTGCGATCAGGTG-GCACCT; SEQ ID NO:6). The presence of the hygromycin cassette from the targeting vector was confirmed using primers HYGF (TGCGGCCGATCTTAGCC; SEQ ID NO:7) and HYGR (TTGACCGATTCCTTGCGG; SEQ ID NO:8) and probe HYGP (ACGAGCGGGTTCGGCCCATTC; SEQ ID NO:9). The nucleotide sequence across the upstream deletion point (SEQ ID NO:10) included the following, which indicates endogenous mouse sequence upstream of the deletion point (contained within the parentheses below) linked contiguously to cassette sequence present at the deletion point: (TTTGTAAACA AAGTCTACCC AGAGACAGAT GACA-GACTTC AGCTCCAATG CTGATTGGTT CCTCACT-TGG GACCAACCCT) CTCGAGTACC GTTCGTATAA TGTATGCTAT ACGAAGTTAT ATGCATCCGG GTAGGGGAGG. The nucleotide sequence across the downstream deletion point (SEQ ID NO:11) included the following, which indicates cassette sequence contiguous with endogenous mouse sequence downstream of the deletion point (contained within the parentheses below): CCTCGAC-CTG CAGCCCTAGG ATAACTTCGT ATAATGTATG CTATACGAAC GGTAGAGCTC (CACAGGCATT TGGGTGGGCA GGGATGGACG GTGACTGGGA CAATCGGGAT GGAAGAGCAT AGAATGGGAG TTAGGGAAGA). Positive ES cell clones were then used to implant female mice using the VELOCIMOUSE® method (described below) to generate a litter of pups containing a deletion of the endogenous MHC class II locus.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses, Nature Biotech. 25(1):91-99). Mice bearing a deletion of H-2Ab1, H-2Aa, H-2Eb1, H-2Eb2, and H-2Ea genes in the endogenous MHC class II locus were identified by genotyping using a modification of allele assay (Valenzuela et al., supra) that detected the presence of the hygromycin cassette and confirmed the absence of endogenous MHC class II sequences.

Mice bearing a deletion of H-2Ab1, H-2Aa, H-2Eb1, H-2Eb2, and H-2Ea genes in the endogenous MHC class II locus can be bred to a Cre deletor mouse strain (see, e.g., International Patent Application Publication No. WO 2009/114400) in order to remove any loxed hygromycin cassette introduced by the targeting vector that is not removed, e.g., at the ES cell stage or in the embryo. Optionally, the hygromycin cassette is retained in the mice.

Example 2

Generation of Large Targeting Vector (LTVEC) Comprising Humanized H-2Eb1 and H-2Ea Genes A targeting vector to introduce humanized MHC II sequences was designed as depicted in FIG. 4. Using VELOCIGENE® genetic engineering technology, Bacterial Artificial Chromosome (BAC) RP23-458122 DNA was modified in various steps to: (1) create a vector comprising a functional I-E α exon 1 from BALB/c H-2Eα gene (FIG. 4A); (2) create a vector comprising replacement of exons 2 and 3 of mouse I-E β gene with those of human DRβ1*04 and replacement of exons 2 and 3 of mouse I-E α with those of human DRα1*01 (FIG. 4B); (3) create a vector carrying exons 2 and 3 of human DRβ1*04 amongst remaining mouse I-E β exons, and exons 2 and 3 of human DRα1*01 amongst remaining mouse I-E a exons including a functional I-E α exon 1 from BALB/c mouse (step (1) (FIG. 4C); and (4) remove a cryptic splice site in the vector generated in (3) (FIG. 4D).

Figure 4A:
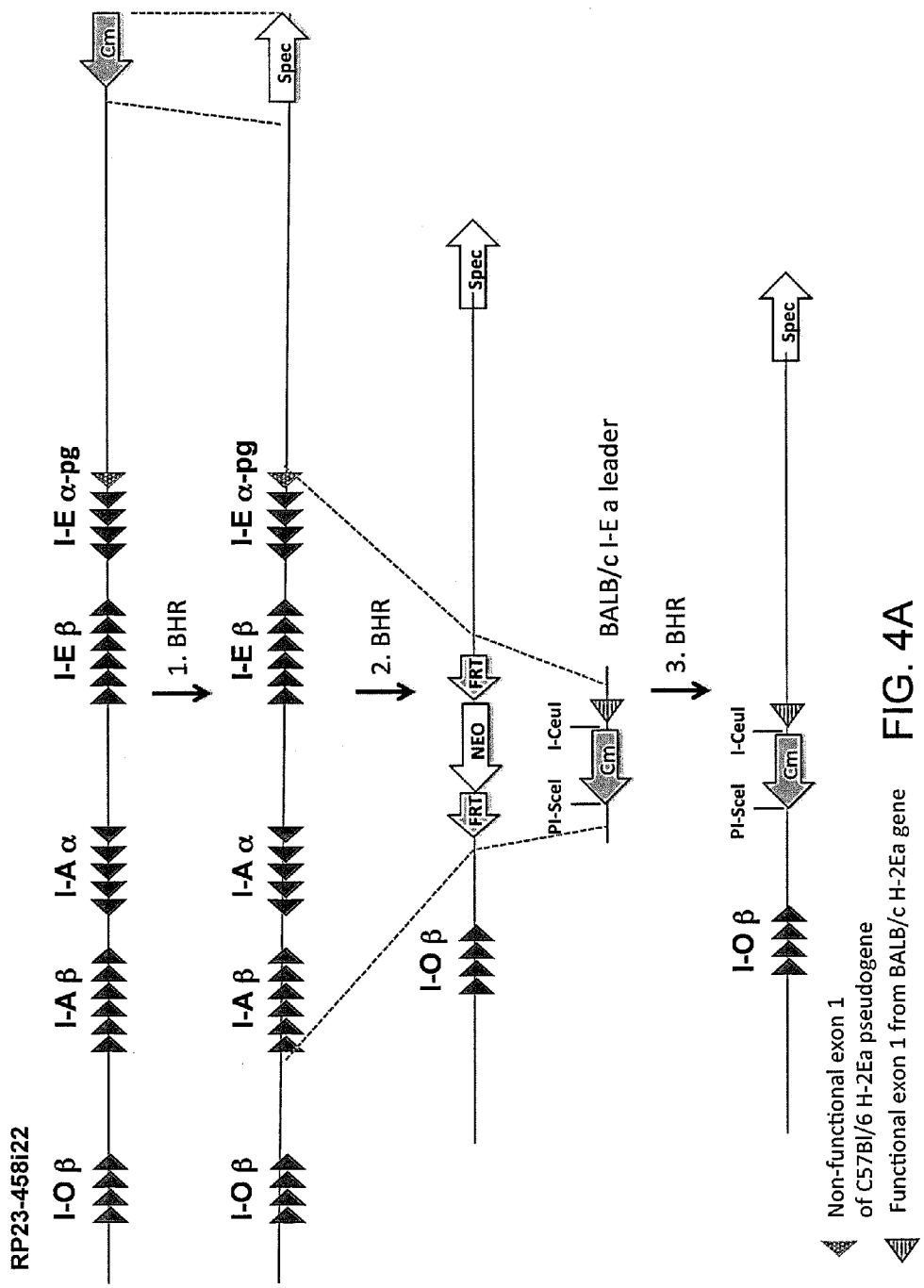
FIG. 4 (A-D) is a schematic illustration (not to scale) of the strategy for generating a targeting vector comprising humanized I-E β and I-E α (i.e., H-2Eβ/HLA-DRβ1*04 and H-2Eα/HLA-DRα*01 chimera, respectively).
In FIG. 4C, the final humanized MHC II sequence from FIG. 4B is ligated between PI-SceI and I-CeuI restriction sites of the final construct from FIG. 4A, to generate a construct comprising humanized MHC II and exon 1 of I-Eα from BALB/c. Pg=pseudogene; BHR=bacterial homologous recombination; CM=chloramphenicol; spec=spectinomycin; hyg=hygromycin; neo=neomycin; EP=electroporation. Triangles represent exons, filled triangles represent mouse exons from C57BL/6 mouse (with the exception of hashed triangles, which represent exon 1 of I-Eα from BALB/c mouse) and open triangles represent human exons.

Specifically, because in the C57Bl/6 mice, the I-E a gene is a pseudogene due to the presence of a non-functional exon 1, first, a vector comprising a functional I-E α exon 1 from BALB/c H-2Ea gene was created (FIG. 4A). RP23-458i22 BAC was modified by bacterial homologous recombination (1.BHR) to replace chloramphenicol resistance gene with that of spectromycin. The resultant vector was further modified by BHR to replace the entire I-A and I-E coding region with a neomycin cassette flanked by recombination sites (2.BHR). Another round of BHR (3. BHR) with the construct comprising an exon encoding BALB/c I-Eα leader (exon 1) and chloramphenicol gene flanked by PI-SceI and I-CeuI restriction sites resulted in a vector comprising a functional BALB/c H-2Ea exon 1.

Figure 4B:
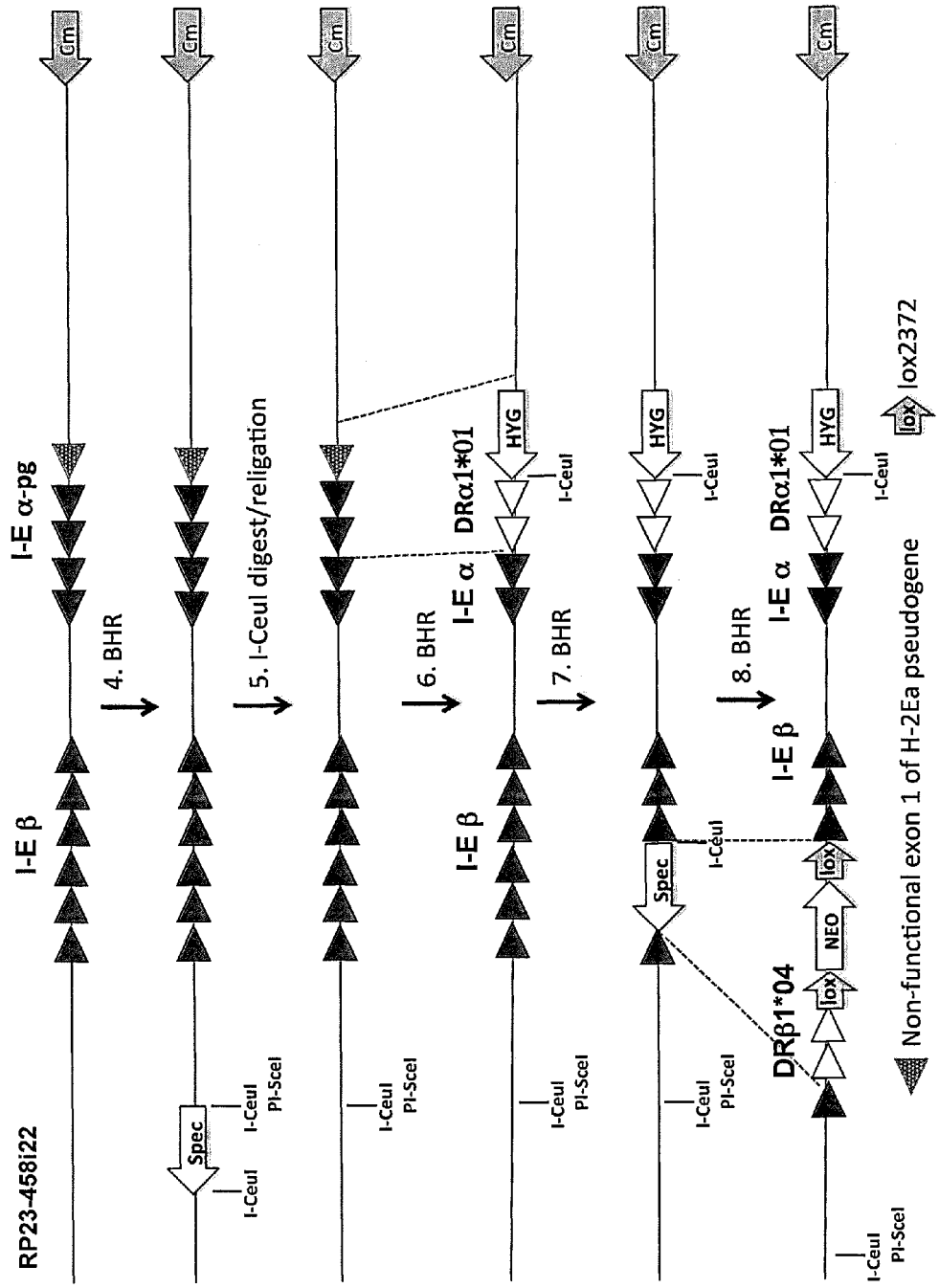

Independently, in order to generate a vector comprising replacement of exons 2 and 3 of mouse I-E β gene with those of human DRβ1*04 and replacement of exons 2 and 3 of mouse I-E a with those of human DRα1*01, RP23-458i22 BAC was modified via several homologous recombination steps, 4. BHR -8. BHR (FIG. 4B). The resultant nucleic acid sequence was flanked by PI-SceI/I-CeuI restriction sites to allow ligation into the construct carrying BALB/c I-Eα exon 1, mentioned above (FIG. 4C).

Figure 4C:
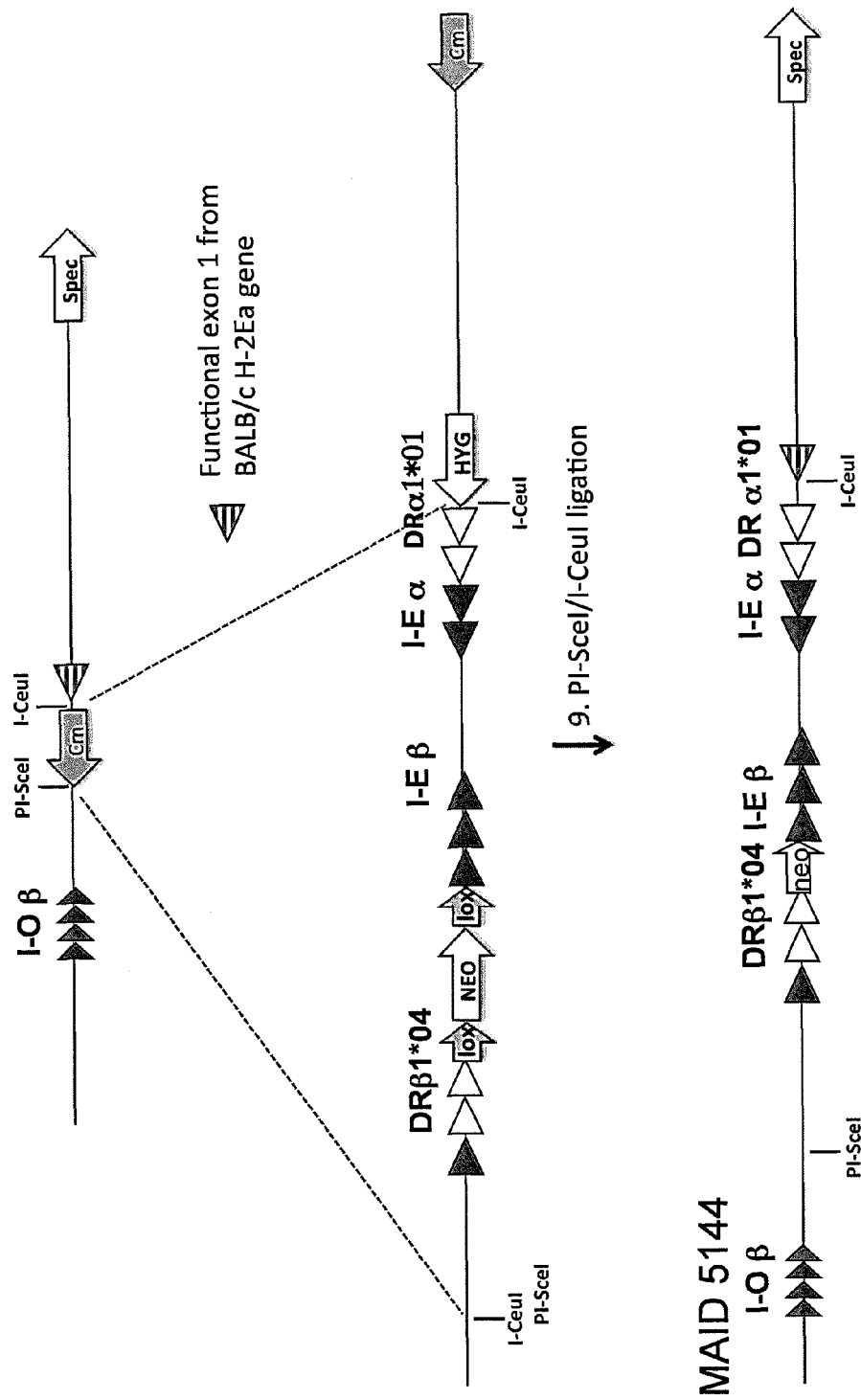
Figure 4D:
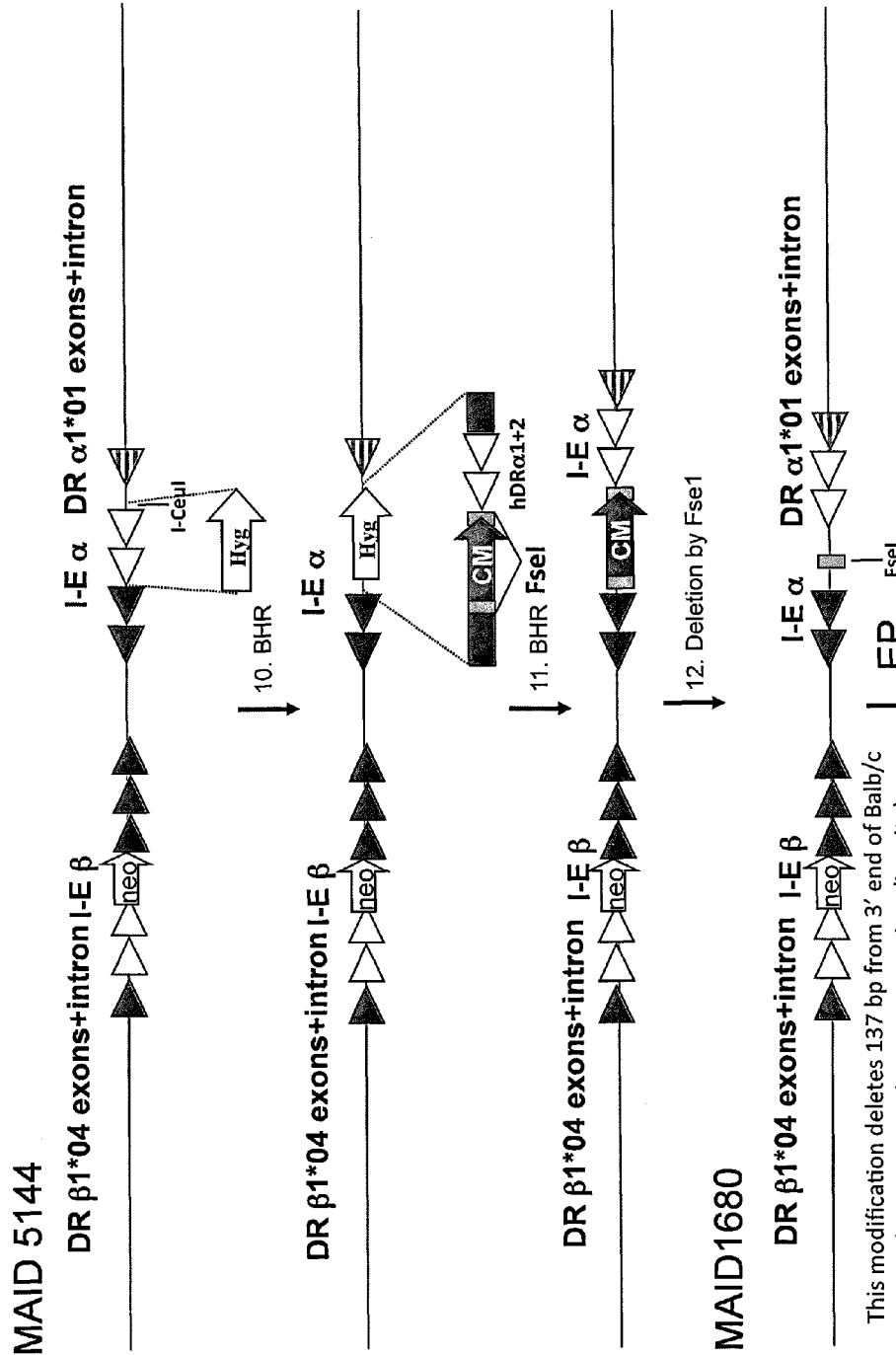

The sequence of the final construct depicted in FIG. 4C contained a cryptic splice site at the 3' end of the BALB/c intron. Several BHR steps (11. BHR-12. BHR) followed by a deletion step were performed to obtain the final targeting vector (MAID 1680) that was used to electroporate into ES cells (FIG. 4D).

In detail, the final targeting vector (MAID 1680), from 5' to 3', was comprised of a 5' mouse homology arm consisting of ~26 kb of mouse genomic sequence ending just upstream of the H-2Ab1 gene of the endogenous MHC class II locus; an ~59 kb insert containing the humanized MHC II β chain gene (humanized H-2Eb1 gene) and humanized MHC II α chain gene (humanized H-2Ea gene) and a floxed neomycin cassette; and a 3' mouse homology arm consisting of ~57 kb of mouse genomic sequence beginning just downstream of the H-2Ea gene of the endogenous MHC class II locus. The nucleotide sequence across the junction between the 5' arm and the insert (SEQ ID NO:12) included the following: (TGCTGATTGG TTCCTCACTT GGGACCAACC C) TAAGCTTTA TCTATGTCGG GTGCGGAGAA AGAGG-TAATG AAATGGCACA AGGAGATCAC ACACCCAAAC CAAACTCGCC, where the italicized sequence is a unique PI-SceI site, and mouse genomic sequence in the 5' homology arm is in parentheses. The nucleotide sequence across the junction between the insert and the 3' arm (SEQ ID NO:13) included the following: CACATCAGTG AGGCTAGAAT AAATTAAAAT CGCTAATATG AAAATGGGG (ATTTG-TACCT CTGAGTGTGA AGGCTGGGAA GACTGCTTTC AAGGGAC), where the mouse genomic sequence in the 3' homology arm is in parentheses.

Within the ~59 kb insert, the H-2Eb1 gene was modified as follows: a 5136 bp region of H-2Eb1, including the last 153 bp of intron1, exon 2, intron 2, exon 3, and the first 122 bp of intron 3, was replaced with the 3111 bp homologous region of human HLA-DRB1*04, including the last 148 bp of intron 1, exon 2, intron 2, exon 3, and the first 132 bp of intron 3. At the junction between the human and mouse sequences of intron 3, a cassette consisting of a 5' lox2372 site, UbC promoter, neomycin resistance gene, and a 3' lox2372 site, was inserted. The resulting gene encoded a chimeric HLA-DRB1*04/H-2Eb1 protein comprised of the mouse H-2Eb1 leader, the human β1 and β2 domains from DRB1*04, and the mouse transmembrane domain and cytoplasmic tail. The nucleotide sequence across the mouse/human junction in intron 1 (SEQ ID NO:14) included the following: (TCCATCACTT CACTGGGTAG CACAGCTGTA ACTGTCCAGC CTG) GGTACCGAGC TCGGATCCAC TAGTAACGGC CGC-CAGTGTG CTGGAATTC GCCCTTGATC GAGCTC-CCTG GGCTGCAGGT GGTGGGCGTT GCGGGTGGGG CCGGTTAA, where the italicized sequence is a multiple cloning site introduced during the cloning steps, and the mouse intron 1 sequences are in parentheses. The nucleotide sequence across the junction between the human intron 3 and neomycin cassette (SEQ ID NO:15) included the following: (ATCTCCATCA GAAGGGCACC GGT) ATAACTT CGTATAAGGT ATCCTATACG AAGTTATATG CATGGC-CTCC GCGCCGGGTT, where the 5' lox2372 site is italicized, and human intron 3 sequence is in parentheses. The nucleotide sequence across the junction between the neomycin cassette and mouse intron 3 (SEQ ID NO:16) included the following: ATAACTTCGT ATAAGGTATC CTATACGAAG TTATCTCGAG (TGGCTTACAG GTAGGTGCGT GAAGCTTCTA CAAGCACAGT TGCCCCCTGG), where the 3' lox2372 site is italicized, and the mouse intron 3 sequence is in parentheses.

Also within the ~59 kb insert, the H-2Ea gene was modified as follows: a 1185 bp region of H-2Ea, including the last 101 bp of intron1, exon 2, intron 2, exon 3, and the first 66 bp of intron 3, was replaced with the 1189 bp homologous region of human HLA-DRA1*01, including the last 104 bp of intron 1, exon 2, intron 2, exon 3, and the first 66 bp of intron 3. As described above, because exon 1 of the C57BL/6 allele of H-2Ea contains a deletion which renders the gene nonfunctional, H-2Ea exon 1 and the remainder of intron 1 were replaced with the equivalent 2616 bp region from the BALB/c allele of H-2Ea, which is functional. The resulting gene encoded a chimeric H-2Ea/HLA-DRA1*01 protein comprised of the mouse H-2Ea leader from BALB/c, the human α1 and α2 domains from DRA1*01, and the mouse transmembrane domain and cytoplasmic tail. The nucleotide sequence across the mouse/human junction in intron 1 (SEQ ID NO:17) included the following: (CTGTTTCTTC CCTAACTCCC ATTCTATGCT CTTCCATCCC GA) CCGCGGCCCA ATCTCTCTCC ACTACTTCCT GCCTA-CATGT ATGTAGGT, where the italicized sequence is a restriction enzyme site introduced during the cloning steps, and the BALB/c intron 1 sequences are in parentheses. The nucleotide sequence across the human/mouse junction in intron 3 (SEQ ID NO:18) included the following: CAAG-GTTTCC TCCTATGATG CTTGTGTGAA ACTCGGGGCC GGCC (AGCATTTAAC AGTACAGGGA TGGGAGCACA GCTCAC), where the italicized sequence is a restriction enzyme site introduced during the cloning steps, and the mouse intron 3 sequences are in parentheses. The nucleotide sequence across the C57BL/6-BALB/c junction 5' of exon 1 (SEQ ID NO:19) included the following: (GAAAGCAGTC TTCCCAGCCT TCACACTCAG AGG-TACAAAT) CCCCATTTTC ATATTAGCGA TTT-TAATTTA TTCTAGCCTC, where the C57BL/6-specific sequences are in parentheses. The nucleotide sequence across the BALB/c-057BL/6 junction 3' of exon 1 (SEQ ID NO:20) included the following: TCTTCCCTAA CTCCCATTCT ATGCTCTTCC ATCCCGA CCG CGG (CCCAATC TCTCTCCACT ACTTCCTGCC TACATGTATG), where SacII restriction site is italicized, and C57BL/6 sequences are in parenthesis.

Example 3

Generation of Humanized MHC II Mice

Figure 8:
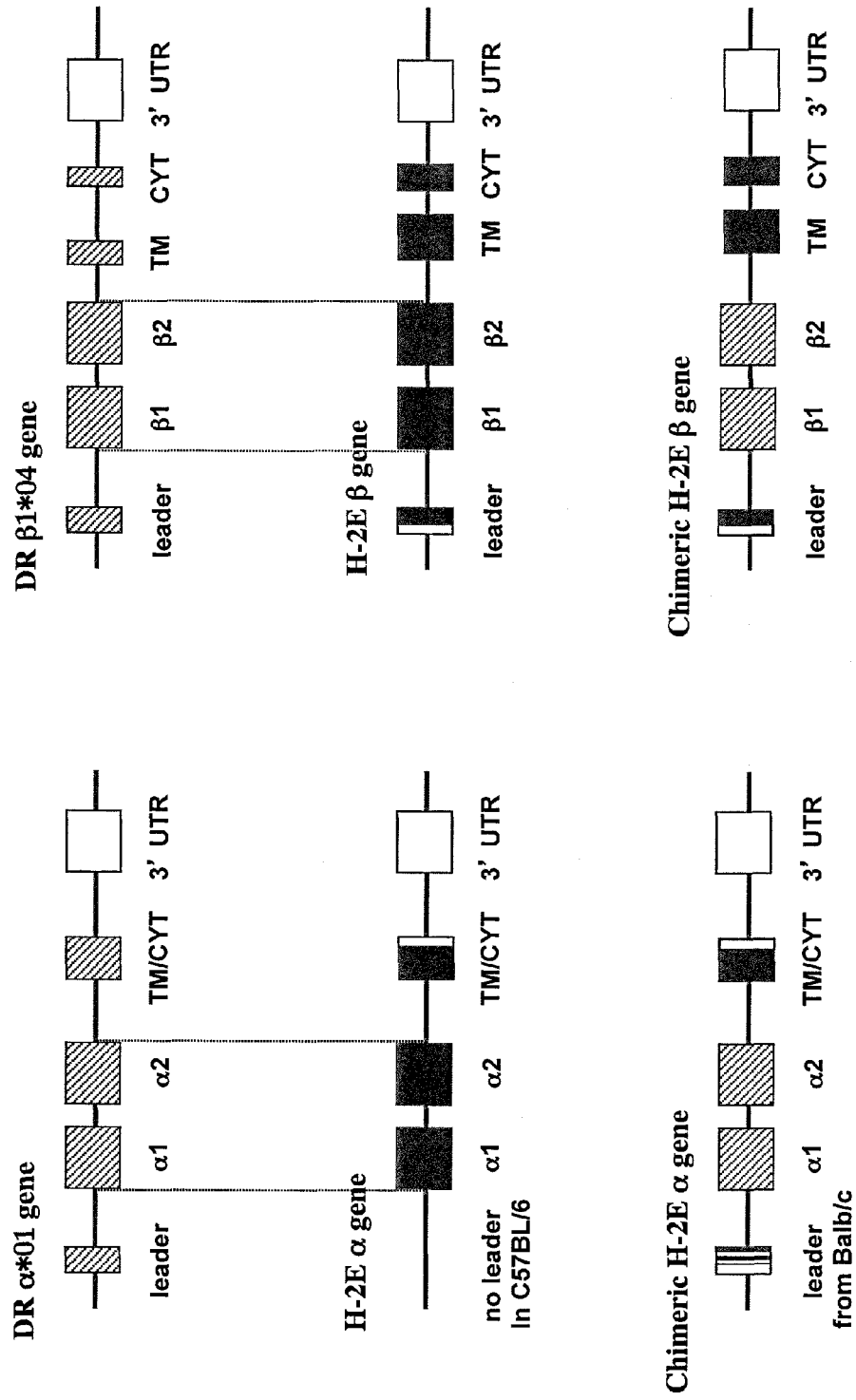
FIG. 8, at left panel, is a schematic illustration (not to scale) of humanization strategy for the MHC II α chain; in particular, the figure shows a replacement of α1 and α2 domains, encoded by exons 2 and 3 of MHC II α gene, while retaining mouse transmembrane and cytoplasmic tail sequences. In the humanized locus, the MHC II α leader sequence is derived from the mouse BALB/c strain. The right panel illustrates humanization of the MHC II β chain; in particular, the figure shows a replacement of β1 and β2 domains, encoded by exons 2 and 3 of MHC II β gene, while retaining the mouse leader and mouse transmembrane and cytoplasmic tail sequences. Top row are all human sequences; middle row are all mouse sequences; bottom row are all humanized sequences, with exons 2 and 3 derived from human HLA-DR genes.

Simplified diagrams of the strategy for generating humanized MHC II mice using the vector of Example 2 are presented in FIGS. 5 and 8.

Specifically, MAID1680 BAC DNA (described above) was used to electroporate MAID5111 ES cells to create modified ES cells comprising a replacement of the endogenous mouse I-A and I-E loci with a genomic fragment comprising a chimeric human DR4/mouse I-E locus. Positive ES cells containing deleted endogenous I-A and I-E loci replaced by a genomic fragment comprising a chimeric human DR4/mouse I-E locus were identified by a quantitative PCR assay using TAQMAN™ probes (Lie and Petropoulos, supra). The insertion of the human DRα sequences was confirmed by PCR using primers hDRA1F (CTGGCGGCTTGAA-GAATTTGG; SEQ ID NO:21), hDRA1R (CATGATTTC-CAGGTTGGCTTTGTC; SEQ ID NO:22), and probe hDRA1P (CGATTTGCCAGCTTTGAGGCTCAAGG; SEQ ID NO:23). The insertion of the human DRβ sequences was confirmed by PCR using primers hDRB1F (AGGCT-TGGGTGCTCCACTTG; SEQ ID NO:24), hDRB1R (GAC-CCTGGTGATGCTGGAAAC; SEQ ID NO:25), and probe hDRB1P (CAGGTGTAAACCTCTCCACTCCGAGGA; SEQ ID NO:26). The loss of the hygromycin cassette from the targeting vector was confirmed with primers HYGF (TGCG-GCCGATCTTAGCC; SEQ ID NO:7) and HYGR (TTGAC-CGATTCCTTGCGG; SEQ ID NO:8) and probe HYGP (AC-GAGCGGGTTCGGCCCATTC; SEQ ID NO:9).

Positive ES cell clones were then used to implant female mice using the VELOCIMOUSE® method (supra) to generate a litter of pups containing a replacement of the endogenous I-A and I-E loci with a chimeric human DR4/mouse I-E locus. Targeted ES cells described above were used as donor ES cells and introduced into an 8-cell stage mouse embryo by the VELOCIMOUSE® method. Mice bearing a chimeric human DR4/mouse I-E locus were identified by genotyping using a modification of allele assay (Valenzuela et al., supra) that detected the presence of a chimeric human DR4/mouse I-E locus.

Figure 6:
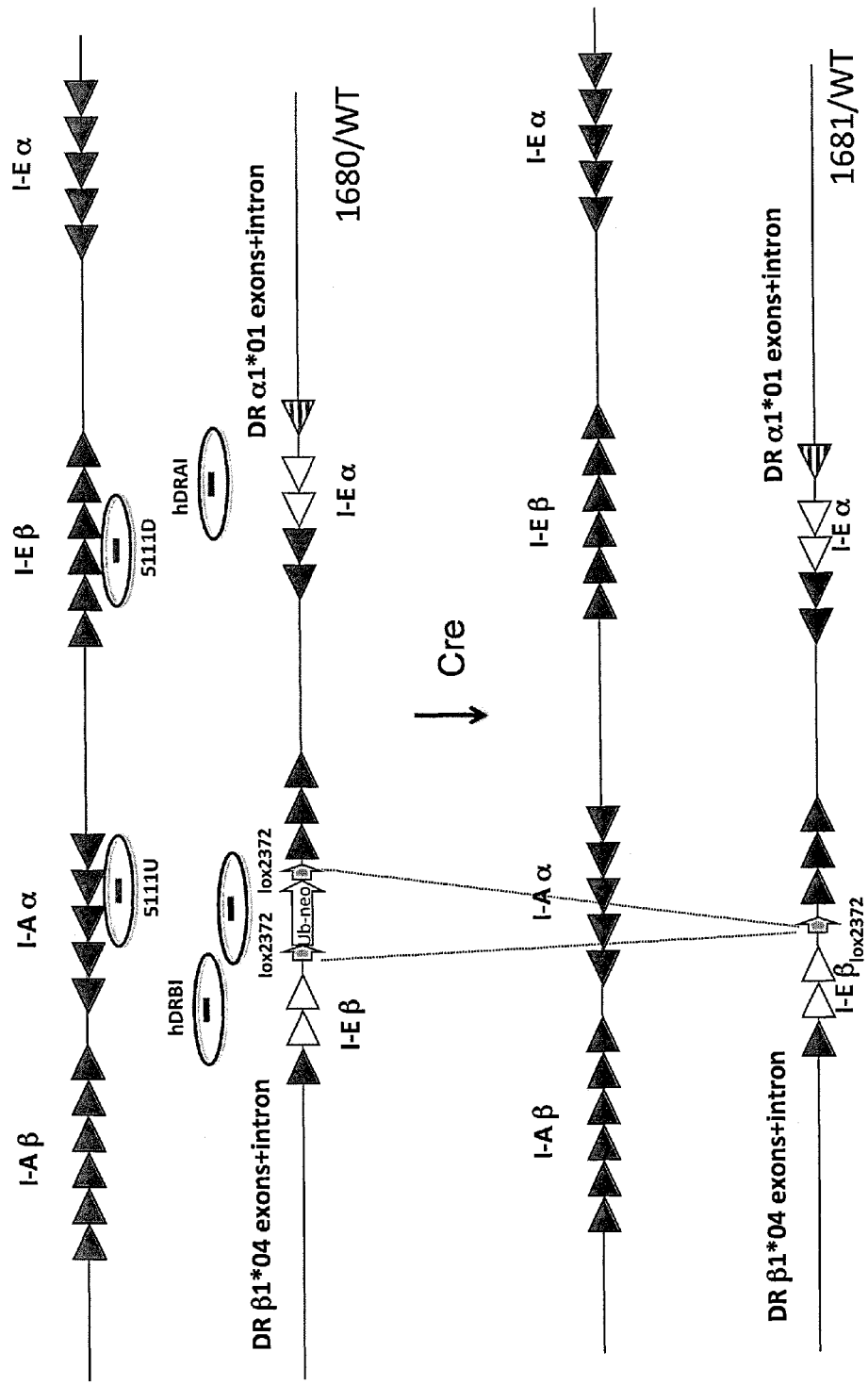
FIG. 6 shows a schematic illustration, not to scale, of Cre-mediated removal of the neomycin cassette of FIG. 5. Open triangles represent human exons; filled triangles represent mouse exons. Top two strands represent MHC II loci in humanized MHC II heterozygous mouse harboring a neomycin selection cassette, and bottom two strands represent MHC II loci in humanized MHC II heterozygous mouse with neomycin cassette removed.
Figure 7:
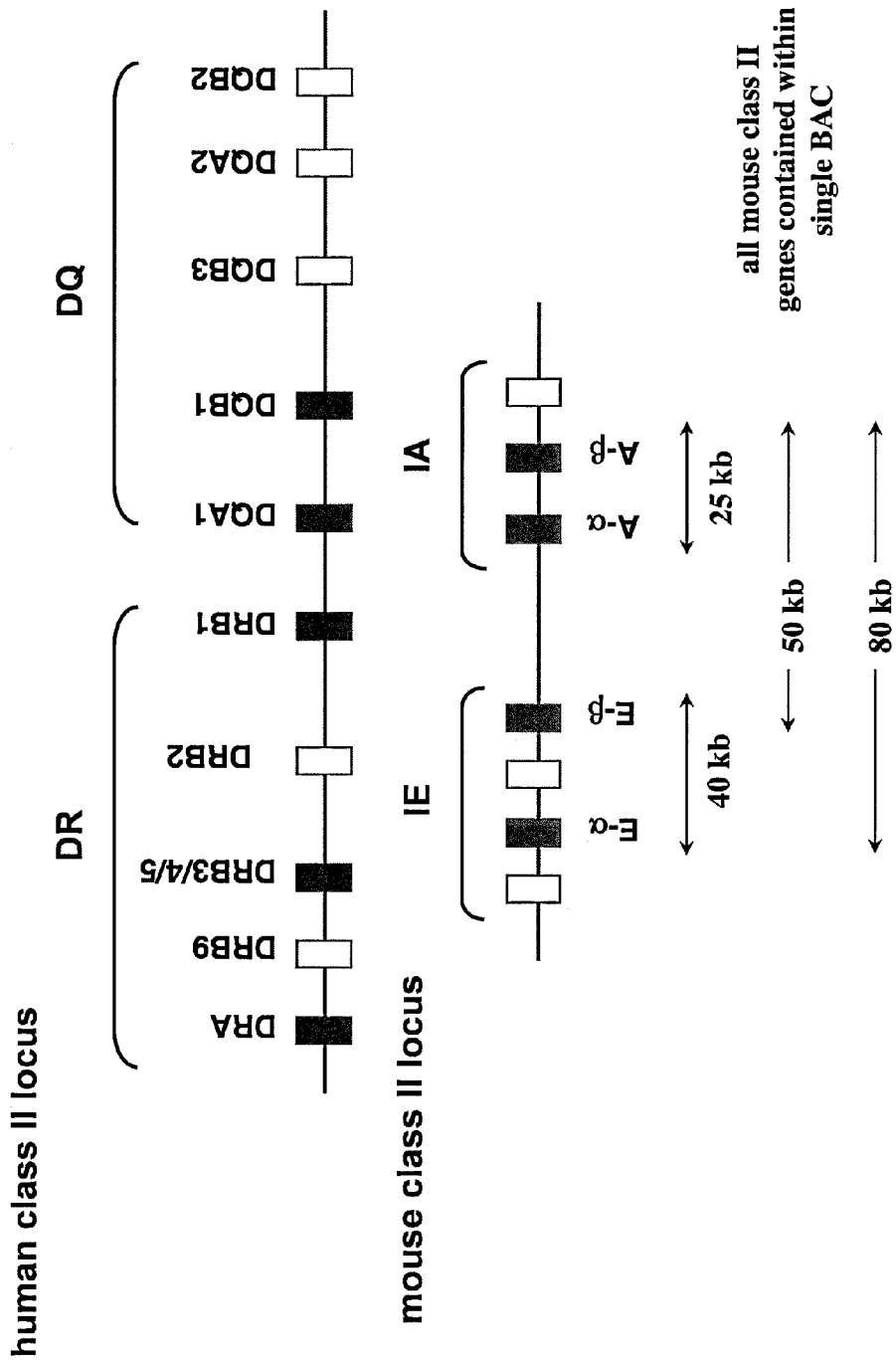
FIG. 7 shows a schematic comparative illustration, not to scale, of mouse and human class II loci. Class II genes are represented by boxes, and empty boxes represent pseudogenes. Relative sizes (kb) of various nucleic acid fragments are included.

Mice bearing a chimeric human DR4/mouse I-E locus can be bred to a Cre deletor mouse strain (see, e.g., International Patent Application Publication No. WO 2009/114400) in order to remove any loxed neomycin cassette introduced by the targeting vector that is not removed, e.g., at the ES cell stage or in the embryo (See FIG. 6).

Example 4

Expression of the Chimeric HLA-DR4 in Genetically Modified Mice

Figure 9:
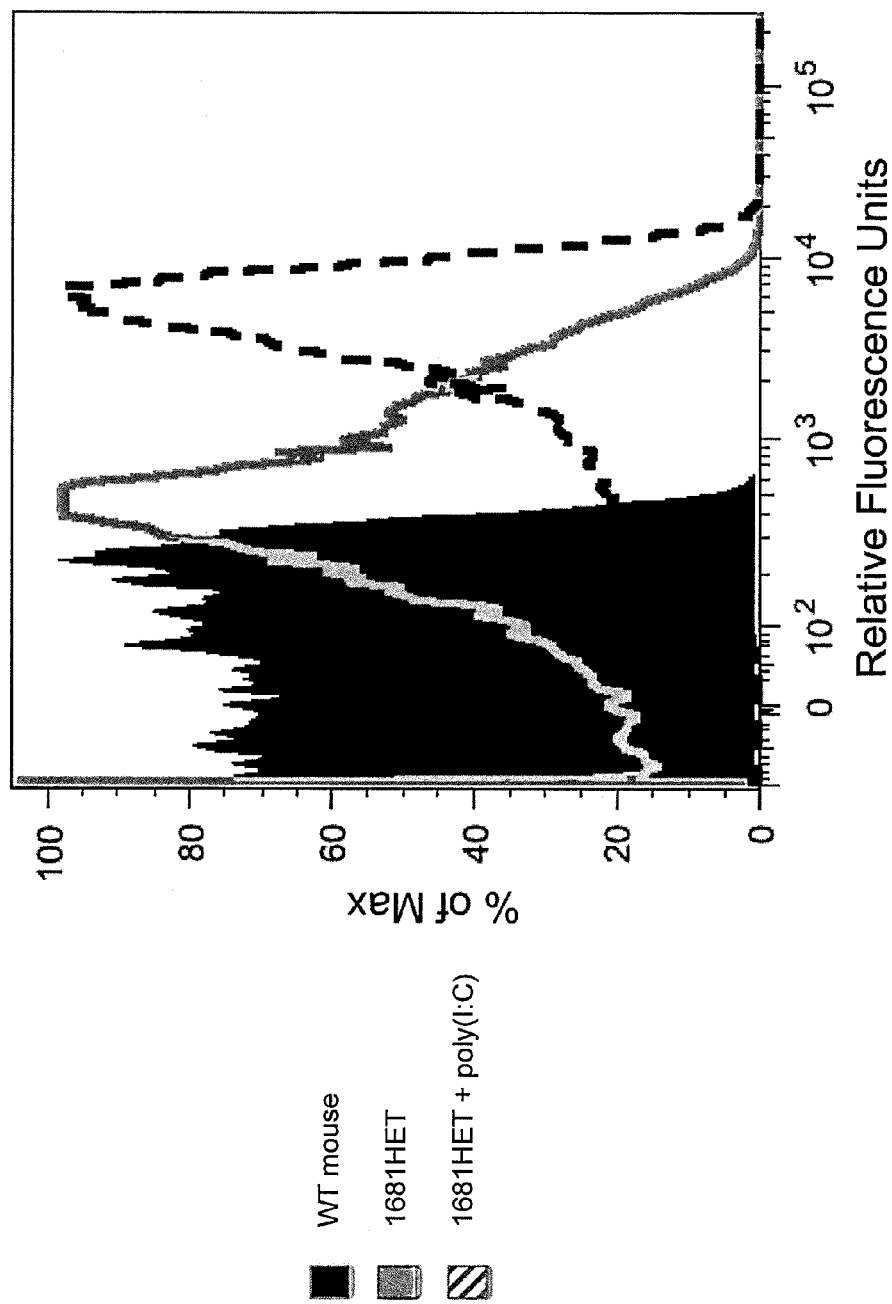
FIG. 9 shows FACS analysis with anti-HLA-DR antibody of B cells from a mouse heterozygous for a chimeric HLA-DR4 (neo cassette removed) in the presence (1681 HET+poly (I:C) or absence (1681HET) of poly(I:C), and a wild-type mouse (WT mouse).

Spleens from WT or heterozygous humanized HLA-DR4 mice ("1681 HET") were perfused with Collagenase D (Roche Bioscience) and erythrocytes were lysed with ACK lysis buffer. Splenocytes were cultured for two days with 25 micrograms/mL poly(I:C) to stimulate the expression of MHC-II genes. Cell surface expression of human HLA-DR4 was analyzed by FACS using fluorochrome-conjugated anti-CD3 (17A2), anti-CD19 (1D3), anti-CD11c (N418), anti-F480 (BM8), anti-I-A/I-E (M15) and anti-HLADR (L243). Flow cytometry was performed using BD-LSRII. Expression of human HLA-DR4 was clearly detectable on the surface of CD19+ B cells and was significantly upregulated upon stimulation by toll-like receptor agonist poly(I:C) (see FIG. 9).

EQUIVALENTS

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A mouse comprising at an endogenous Major Histocompatibility Complex (MHC) II gene locus a first nucleotide sequence encoding a chimeric human/mouse MHC II α polypeptide and a second nucleotide sequence encoding a chimeric human/mouse MHC II β polypeptide, wherein a human portion of the chimeric human/mouse MHC II α polypeptide comprises a human MHC II α2 domain and a human portion of the chimeric human/mouse MHC II β polypeptide comprises a human MHC II β2 domain, wherein the first nucleotide sequence is expressed under regulatory control of an MHC II α promoter, and the second nucleotide sequence is expressed under regulatory control of an MHC II β promoter, and wherein the mouse expresses the chimeric human/mouse MHC II α and β polypeptides on the surface of an antigen presenting cell of the mouse.

2. The mouse of claim 1, wherein the chimeric human/mouse MHC II α polypeptide further comprises a human α1 domain.

3. The mouse of claim 1, wherein the chimeric human/mouse MHC II β polypeptide further comprises a human β1 domain.

4. The mouse of claim 1, wherein the first nucleotide sequence is expressed under regulatory control of endogenous mouse MHC II α promoter and regulatory elements, and the second nucleotide sequence is expressed under regulatory control of endogenous mouse MHC II β promoter and regulatory elements.

5. The mouse of claim 1, wherein a mouse portion of the chimeric human/mouse MHC II α polypeptide comprises transmembrane and cytoplasmic domains of an endogenous mouse MHC II α polypeptide.

6. The mouse of claim 1, wherein a mouse portion of the chimeric human/mouse MHC II β polypeptide comprises transmembrane and cytoplasmic domains of an endogenous mouse MHC II β polypeptide.

7. The mouse of claim 1, wherein the human portion of the chimeric human/mouse MHC II α polypeptide is encoded by a Human Leukocyte Antigen (HLA) class II gene selected from the group consisting of any α chain gene of HLA-DR, HLA-DQ, and HLA-DP; and wherein the human portion of the chimeric human/mouse MHC β polypeptide is encoded by a HLA class II gene selected from the group consisting of any β chain gene of HLA-DR, HLA-DQ, and HLA-DP.

8. The mouse of claim 7, wherein the human portion of the chimeric human/mouse MHC II α polypeptide is encoded by a human HLA-DRA gene and the human portion of the chimeric human/mouse MHC II β polypeptide is encoded by a human HLA-DRB1*04 gene.

9. The mouse of claim 1, wherein the mouse portion of the chimeric human/mouse MHC II α polypeptide comprises cytoplasmic and transmembrane domains from a mouse H-2E α polypeptide, and the mouse portion of the chimeric human/mouse MHC II β polypeptide comprises cytoplasmic and transmembrane domains from a mouse H-2E β polypeptide.

10. The mouse of claim 1, wherein the mouse does not express functional endogenous MHC II polypeptides from their endogenous mouse MHC II loci.

11. A mouse comprising at an endogenous mouse Major Histocompatibility Complex (MHC) II locus a first nucleotide sequence encoding a chimeric human/mouse MHC II α polypeptide and a second nucleotide sequence encoding a chimeric human/mouse MHC II β polypeptide,
wherein a human portion of the chimeric MHC II α polypeptide comprises a human α2 domain encoded by a human HLA-DRA gene and the human portion of the chimeric MHC II β polypeptide comprises a human β2 domain encoded by a human HLA-DRB gene,
wherein a mouse portion of the chimeric MHC II α polypeptide comprises transmembrane and cytoplasmic domains of a mouse H-2E α chain and a mouse portion of the chimeric MHC II β polypeptide comprises transmembrane and cytoplasmic domains of a mouse H-2E β chain,
wherein the first nucleotide sequence is expressed under regulatory control of an MHC II α promoter and the second nucleotide sequence is expressed under regulatory control of an MHC II β promoter,
and wherein the mouse expresses a chimeric HLA-DR/H-2E MHC II polypeptide on the surface of an antigen presenting cell of the mouse.

12. The mouse of claim 11, wherein the extracellular domain of the α polypeptide further comprises a human α1 domain encoded by a human HLA-DRA gene.

13. The mouse of claim 11, wherein the extracellular domain of the β polypeptide further comprises a human β1 domain encoded by a human HLA-DRB gene.

14. The mouse of claim 11, wherein the first nucleotide sequence is expressed under regulatory control of endogenous mouse MHC II α promoter and regulatory elements, and the second nucleotide sequence is expressed under regulatory control of endogenous mouse MHC II β promoter and regulatory elements.

15. The mouse of claim 11, wherein the mouse does not express functional endogenous MHC II polypeptides from their endogenous mouse loci.

16. The mouse of claim 11, wherein the mouse expresses a chimeric HLA-DR4/H-2E MHC II polypeptide.

* * * * *

UNITED STATES PATENT AND TRADEMARK OFFICE
CERTIFICATE OF CORRECTION

PATENT NO.         : 8,847,005 B2
APPLICATION NO.    : 13/661116
DATED              : September 30, 2014
INVENTOR(S)        : Lynn Macdonald et al.

Page 1 of 1

It is certified that error appears in the above-identified patent and that said Letters Patent is hereby corrected as shown below:

Title Page,
Item (12), "United States Patent MacDonald et al."
should read --United States Patent Macdonald et al.--

Item (75), Inventors: "Lynn MacDonald, White Plains, NY (US); Andrew J. Murphy, Croton-on-Hudson, NY (US); Naxin Tu, Pleasantville, NY; Cagan Gurer, Valhalla, NY; Vera Voronina, Thornwood, NY; Sean Stevens, San Francisco, CA"
should read --Lynn Macdonald, White Plains, NY (US); Andrew J. Murphy, Croton-on-Hudson, NY (US); Naxin Tu, Pleasantville, NY; Cagan Gurer, Valhalla, NY; Vera Voronina, Thornwood, NY; Sean Stevens, San Francisco, CA--

Signed and Sealed this
Thirty-first Day of March, 2015

Michelle K. Lee
*Director of the United States Patent and Trademark Office*